US011952416B2

(12) United States Patent
Han

(10) Patent No.: US 11,952,416 B2
(45) Date of Patent: Apr. 9, 2024

(54) ANTI-ANNEXIN A1 ANTIBODIES

(71) Applicant: The Trustees of Columbia University in the City of New York, New York, NY (US)

(72) Inventor: Yiping Han, Paramus, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/467,405

(22) Filed: Sep. 14, 2023

(65) Prior Publication Data

US 2024/0002487 A1    Jan. 4, 2024

Related U.S. Application Data

(63) Continuation of application No. PCT/US2022/023429, filed on Apr. 5, 2022.

(60) Provisional application No. 63/172,961, filed on Apr. 9, 2021.

(51) Int. Cl.
*C07K 16/18*    (2006.01)
(52) U.S. Cl.
CPC .......... *C07K 16/18* (2013.01); *C07K 2317/24* (2013.01); *C07K 2317/565* (2013.01)

(58) Field of Classification Search
None
See application file for complete search history.

(56) References Cited

FOREIGN PATENT DOCUMENTS

| WO | WO 2017/160725 A2 | 9/2017 |
| WO | WO 2018/021972 A9 | 8/2018 |
| WO | WO 2019/222618 A1 | 11/2019 |
| WO | WO 2020/223573 A2 | 11/2020 |

OTHER PUBLICATIONS

International Search Report dated Sep. 8, 2022 in connection with PCT International Application No. PCT/US2022/23429.
Written Opinion of the International Searching Authority dated Sep. 8, 2022 in connection with PCT International Application No. PCT/US2022/23429.

*Primary Examiner* — Aurora M Fontainhas
(74) *Attorney, Agent, or Firm* — Amster, Rothstein & Ebenstein LLP

(57) ABSTRACT

Anti-annexin A1 antibodies are provided and methods of treating FAP and cancer using Anti-annexin A1 antibodies, antibody fragments or fusion proteins, including bispecific antibodies targeting two different annexin A1 epitopes, are also provided.

12 Claims, 16 Drawing Sheets

Specification includes a Sequence Listing.

ANTI-ANNEXIN A1 ANTIBODIES

CROSS-REFERENCE TO RELATED APPLICATIONS

This application is a continuation of PCT International Application No. PCT/US2022/023429, filed Apr. 5, 2022, claiming the benefit of U.S. Provisional Application No. 63/172,961, filed Apr. 9, 2021, the contents of each of which are hereby incorporated by reference into the subject application.

This application incorporates-by-reference nucleotide sequences which are present in the file named "231214 91899 A PCT A Substitute Sequence Listing AWG.xml", which is 61 kilobytes in size, and which was created on Dec. 13, 2023, in the IBM-PC machine format, having an operating system compatibility with MS-Windows, which is contained in the xml file filed Dec. 14, 2023 as part of this application.

STATEMENT OF GOVERNMENTAL INTEREST

This invention was made with government support under DE014924, CA192111, and DE029532 awarded by the National Institutes of Health. The government has certain rights in the invention.

BACKGROUND

Colorectal cancer (CRC) is the second leading cause of cancer death in the United States, affecting 1 in 20 individuals (ACS 2012). CRC has long been recognized to result from host mutations that accumulate over time, developing from precancerous adenomatous polyps into adenocarcinoma over approximately ten years (Vogelstein and Kinzler 1993). Advancements in microbial detection technology and human microbiome research have revolutionized our understanding of a wide spectrum of diseases, including CRC (Dulal and Keku 2014; Keku et al. 2015). However, there is still a need for more effective treatments for CRC, and as well as other solid tumors.

The present invention provides compositions, treatments and methods for treating CRC and other solid tumors, and Familial Adenomatous Polyposis (FAP).

SUMMARY

An antibody which binds annexin A1, or an annexin A1-binding fragment thereof, or an annexin A1-binding fusion protein, comprising:

a)
a heavy chain comprising:
(SEQ ID NO: 2)
CDR1 having the sequence GFTFSDFY;

(SEQ ID NO: 4)
CDR2 having the sequence SKNKANDYTT;

(SEQ ID NO: 6)
CDR3 having the sequence AAGGYDEGVGWYFDV;
and a light chain comprising:
(SEQ ID NO: 8)
CDR1 having the sequence QNVGTN;

(SEQ ID NO: 10)
CDR2 having the sequence SAS;

(SEQ ID NO: 12)
CDR3 having the sequence QQYNNYPYT;
or b)
a heavy chain comprising:
(SEQ ID NO: 14)
CDR1 having the sequence GYTFTNYW;

(SEQ ID NO: 16)
CDR2 having the sequence VYPGGGYI;

(SEQ ID NO: 18)
CDR3 having the sequence ARWGTTVDWYFDV;
and a light chain comprising:
(SEQ ID NO: 20)
CDR1 having the sequence SSVSY;

(SEQ ID NO: 22)
CDR2 having the sequence DTS;

(SEQ ID NO: 24)
CDR3 having the sequence QQWSSNPYT;
or c)
a heavy chain comprising:
(SEQ ID NO: 26)
CDR1 having the sequence GFTFSDYD;

(SEQ ID NO: 28)
CDR2 having the sequence ISDGGSFT;

(SEQ ID NO: 30)
CDR3 having the sequence AKKKGYGDAMDY;
and a light chain comprising:
(SEQ ID NO: 32)
CDR1 having the sequence EDIFIR;

(SEQ ID NO: 34)
CDR2 having the sequence GAT;

(SEQ ID NO: 36)
CDR3 having the sequence QQYWNTPWT.

An antibody which binds annexin A1, or an annexin A1-binding fragment thereof or annexin A1-binding fusion protein, comprising complementary-determining regions CDR1 through CDR6, wherein one or more of CDR1 through CDR6 has 85% or greater identity with, but not 100% identity with, the CDR1 through CDR6 sequences set forth as follows:

e)
a heavy chain comprising:
(SEQ ID NO: 2)
CDR1 having the sequence GFTFSDFY;

(SEQ ID NO: 4)
CDR2 having the sequence SKNKANDYTT;

(SEQ ID NO: 6)
CDR3 having the sequence AAGGYDEGVGWYFDV;
and

-continued a light chain comprising:

CDR4 having the sequence QNVGTN; (SEQ ID NO: 8)

CDR5 having the sequence SAS; (SEQ ID NO: 10)

CDR6 having the sequence QQYNNYPYT; (SEQ ID NO: 12)
or f)
a heavy chain comprising:

CDR 1 having the sequence GYTFTNYW; (SEQ ID NO: 14)

CDR2 having the sequence VYPGGGYI; (SEQ ID NO: 16)

CDR3 having the sequence ARWGTTVDWYFDV; (SEQ ID NO: 18)
and a light chain comprising:

CDR4 having the sequence SSVSY; (SEQ ID NO: 20)

CDR5 having the sequence DTS; (SEQ ID NO: 22)

CDR6 having the sequence QQWSSNPYT; (SEQ ID NO: 24)
or g)
a heavy chain comprising:

CDR1 having the sequence GFTFSDYD; (SEQ ID NO: 26)

CDR2 having the sequence ISDGGSFT; (SEQ ID NO: 28)

CDR3 having the sequence AKKKGYGDAMDY; (SEQ ID NO: 30)
and a light chain comprising:

CDR4 having the sequence EDIFIR; (SEQ ID NO: 32)

CDR5 having the sequence GAT; (SEQ ID NO: 34)

CDR6 having the sequence QQYWNTPWT. (SEQ ID NO: 36)

A pharmaceutical composition comprising:
(i) the antibody, annexin A1-binding fragment, or annexin A1-binding fusion protein as described herein and a carrier; or
(ii) two different antibodies, annexin A1-binding fragments, or annexin A1-binding fusion proteins as described herein and a carrier.

A method of reducing development of or treating a cancer, comprising administering to a subject having the cancer an amount of an antibody which binds annexin A1, or an annexin A1-binding fragment thereof or annexin A1-binding fusion protein as described herein, effective to reduce development of or treat a cancer.

A method of reducing development of and/or treating a Familial Adenomatous Polyposis (FAP) in a subject, comprising administering to a subject having FAP an amount of an antibody which binds annexin A1, or an annexin A1-binding fragment thereof or annexin A1-binding fusion protein as described herein, effective to reduce development of or treat FAP.

A method of reducing development of or treating a solid tumor, comprising administering to a subject having the solid tumor an amount of an antibody which binds annexin A1, or an annexin A1-binding fragment thereof or annexin A1-binding fusion protein as described herein, effective to reduce development of or treat a solid tumor.

A method of reducing development of or treating a cancer or Familial Adenomatous Polyposis (FAP), comprising administering to a subject having the cancer an amount of the pharmaceutical composition as described herein effective to reduce development of or treat a cancer or FAP.

A method of reducing development of or treating a cancer, comprising administering to a subject having the cancer an amount of two different antibodies which bind annexin A1, or two different annexin A1-binding fragments thereof, or two different annexin A1-binding fusion proteins, as described herein, or pharmaceutical composition comprising such, effective to reduce development of or treat a cancer.

A method of reducing development of or treating a Familial Adenomatous Polyposis (FAP), comprising administering to a subject having the FAP an amount of two different antibodies which bind annexin A1, or two different annexin A1-binding fragments thereof, or two different annexin A1-binding fusion proteins, as described herein, or pharmaceutical composition comprising such, effective to reduce development of or treat FAP.

A method of reducing resistance to a chemotherapy for a cancer in a subject, comprising administering to the subject an amount of an antibody which binds annexin A1, or an annexin A1-binding fragment thereof, or annexin A1-binding fusion protein, as described herein or pharmaceutical composition as described herein, effective to reduce resistance to a chemotherapy being administered or to be administered to the subject.

A nucleic acid encoding a heavy chain of an antibody as described herein.

A nucleic acid encoding a light chain an antibody as described herein.

An antibody which binds annexin A1, or an annexin A1-binding fragment thereof, or an annexin A1-binding fusion protein, as described herein, for use as a medicament in treating a cancer or FAP or for reducing resistance to a chemotherapy.

A combination of two or more different antibodies which binds annexin A1, or two or more different annexin A1-binding fragments thereof, or two or more different fusion proteins, as described herein, for use as a medicament in treating a cancer or FAP.

In embodiments, the annexin A1-binding antibody or fragments are inhibitor or antagonistic with respect to annexin A1.

Disclosed herein are anti-annexin monoclonal antibodies which effectively inhibit tumor growth both in vitro and in vivo (xenograft mouse models).

Thus, one embodiment is a monoclonal antibody disclosed herein.

A further embodiment of the present disclosure is a method of treating cancer in a subject in need thereof comprising administering a therapeutically effective amount of one of the monoclonal antibodies which inhibits or blocks annexin A1.

A further embodiment of the present invention is a method of preventing cancer in a subject, in need thereof (i.e., at high risk of developing cancer), comprising administering a therapeutically effective amount of one of the monoclonal antibodies which inhibits or blocks annexin A1.

A subject who would be considered high risk for developing colorectal cancer would include a subject with familial adenomatous polyposis or FAP and a subject at risk for recurrence, such as a subject who has a high level of annexin A1 in their colorectal cancer tissue.

A further embodiment of the present invention is a method of reducing chemo-resistance of cancer in a subject in need thereof comprising administering a therapeutically effective amount of one of the monoclonal antibodies which inhibits or blocks annexin A1.

In some embodiments, the cancer is chosen from the group consisting of melanoma, renal cancer, prostate cancer, pancreatic adenocarcinoma, breast cancer, colon or colorectal cancer (CRC), lung cancer, esophageal cancer, squamous cell carcinoma of the head and neck, liver cancer, ovarian cancer, cervical cancer, thyroid cancer, glioblastoma, glioma, and leukemia.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawing, unless otherwise indicated.

DETAILED DESCRIPTION

Figure 1:
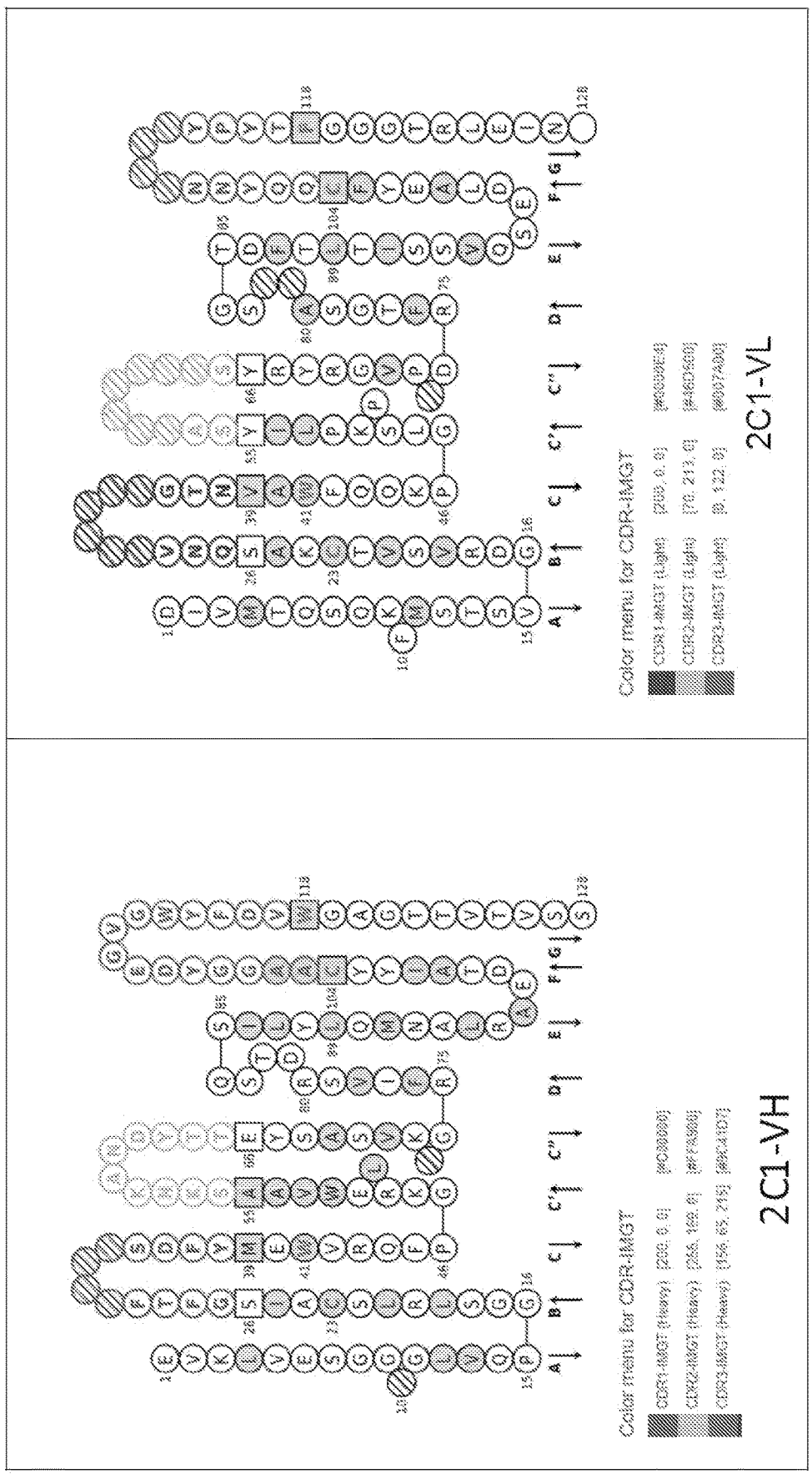
FIG. 1: Diagram of mAb 2C1 sequences (VH SEQ ID NO:37; VL SEQ ID NO:38). Diagonally marked residues in CDRs absent, shown for structural convenience.

An antibody which binds annexin A1, or an annexin A1-binding fragment thereof, or a fusion protein, comprising:

a)
a heavy chain comprising:
```
                                    (SEQ ID NO: 2)
CDR1 having the sequence GFTFSDFY;

(SEQ ID NO: 4)
CDR2 having the sequence SKNKANDYTT;

(SEQ ID NO: 6)
CDR3 having the sequence AAGGYDEGVGWYFDV;
and a light chain comprising:
                                    (SEQ ID NO: 8)
CDR1 having the sequence QNVGTN;

(SEQ ID NO: 10)
CDR2 having the sequence SAS;

(SEQ ID NO: 12)
CDR3 having the sequence QQYNNYPYT;
or b)
a heavy chain comprising:
                                    (SEQ ID NO: 14)
CDR1 having the sequence GYTFTNYW;

(SEQ ID NO: 16)
CDR2 having the sequence VYPGGGYI;

(SEQ ID NO: 18)
CDR3 having the sequence ARWGTTVDWYFDV;
and a light chain comprising:
                                    (SEQ ID NO: 20)
CDR1 having the sequence SSVSY;

(SEQ ID NO: 22)
CDR2 having the sequence DTS;

(SEQ ID NO: 24)
CDR3 having the sequence QQWSSNPYT;
or c)
a heavy chain comprising:
                                    (SEQ ID NO: 26)
CDR1 having the sequence GFTFSDYD;

(SEQ ID NO: 28)
CDR2 having the sequence ISDGGSFT;

(SEQ ID NO: 30)
CDR3 having the sequence AKKKGYGDAMDY;
and a light chain comprising:
                                    (SEQ ID NO: 32)
CDR1 having the sequence EDIFIR;

(SEQ ID NO: 34)
CDR2 having the sequence GAT;
```

In embodiments of the antibody, annexin A1-binding fragment, or fusion protein,

```
the heavy chain comprises:
                                    (SEQ ID NO: 2)
CDR1 having the sequence GFTFSDFY;

(SEQ ID NO: 4)
CDR2 having the sequence SKNKANDYTT;

(SEQ ID NO: 6)
CDR3 having the sequence AAGGYDEGVGWYFDV;
and the light chain comprises:
                                    (SEQ ID NO: 8)
CDR1 having the sequence QNVGTN;

(SEQ ID NO: 10)
CDR2 having the sequence SAS;

(SEQ ID NO: 12)
CDR3 having the sequence QQYNNYPYT.
```

In embodiments of the antibody, annexin A1-binding fragment, or fusion protein, the heavy chain comprises:

```
the heavy chain comprises:
                                    (SEQ ID NO: 14)
CDR1 having the sequence GYTFTNYW;

(SEQ ID NO: 16)
CDR2 having the sequence VYPGGGYI;

(SEQ ID NO: 18)
CDR3 having the sequence ARWGTTVDWYFDV;
and the light chain comprises:
                                    (SEQ ID NO: 20)
CDR1 having the sequence SSVSY;

(SEQ ID NO: 22)
CDR2 having the sequence DTS;

(SEQ ID NO: 24)
CDR3 having the sequence QQWSSNPYT.
```

In embodiments of the antibody, annexin A1-binding fragment, or fusion protein,

```
the heavy chain comprises:
                                    (SEQ ID NO: 26)
CDR1 having the sequence GFTFSDYD;

(SEQ ID NO: 28)
CDR2 having the sequence ISDGGSFT;

(SEQ ID NO: 30)
CDR3 having the sequence AKKKGYGDAMDY;
and the light chain comprises:
                                    (SEQ ID NO: 32)
CDR1 having the sequence EDIFIR;
```

```
                                    (SEQ ID NO: 34)
CDR2 having the sequence GAT;

(SEQ ID NO: 36)
CDR3 having the sequence QQYWNTPWT.
```

In embodiments, the antibody is a monoclonal antibody.

In embodiments the antibody, annexin A1-binding fragment, or fusion protein, comprises framework regions of a light chain and/or a heavy chain which are human framework regions, or have 85% or more sequence identity thereto. In embodiments, the framework regions of the light chain and/or the heavy chain are human framework regions.

In embodiments, the antibody is a humanized antibody.

In embodiments, the antibody or antigen-binding fragment thereof has a human sequence Fc region.

In embodiments, the antibody or fragment thereof is chimeric.

In embodiments, the antibody is a monospecific antibody comprising two heavy chains of identical sequence and two light chains of identical sequence. In embodiments, the fragment is a fragment of a monospecific antibody.

In embodiments, the antibody is a bispecific antibody, or wherein the annexin A1-binding fragment is a fragment of a bispecific antibody, comprising (i) a heavy chain and a light chain as set forth in a), b) or c), and (ii) a heavy chain and a light chain as set forth in a), b) or c) hereinabove,
wherein the heavy chain and a light chain of (i) are different in sequence from the heavy chain and a light chain of (ii). In embodiments, the bispecific antibody or annexin A1-binding fragment comprises (i) a heavy chain and a light chain as set forth in a), and (ii) a heavy chain and a light chain as set forth in b). In embodiments, the bispecific antibody or annexin A1-binding fragment comprises (i) a heavy chain and a light chain as set forth in a), and (ii) a heavy chain and a light chain as set forth in c). In embodiments, the bispecific antibody or annexin A1-binding fragment comprises (i) a heavy chain and a light chain as set forth in b), and (ii) a heavy chain and a light chain as set forth in c).

As used herein, a bispecific antibody includes an antibody which is capable of binding two different epitopes on a single antigen, namely annexin A1.

In embodiments, the bispecific antibody is a bispecific IgG. In embodiments, the bispecific antibody is a KiH, a κλ-body, or a CrossMab.

In embodiments, the antibody is an IgG1(λ) or an IgG2 (λ). In embodiments, the antibody is an IgG4.

In embodiments, annexin A1-binding fragment is an Fab fragment, an Fab' fragment, or an F(ab)' fragment.

In embodiments, the fusion protein is a single chain variable fragment (scFv).

In embodiments, the fusion protein is a BiTE (bispecific T-cell engager) or other tandem scFv, a chemically-linked F(ab')$_2$, a diabody, an IgG-scFv, a TandAb (tandem diabody), a DVD-Ig (dual variable domain immunoglobulin), or a DART (dual-affinity retargeting molecule).

In embodiments, the fusion protein comprises (i) a heavy chain and a light chain as set forth in a), b) or c), and (ii) a heavy chain and a light chain as set forth in a), b) or c), wherein the heavy chain and a light chain of (i) are different in sequence from the heavy chain and a light chain of (ii).

In embodiments, the annexin A1 is encoded by ANXA1, as set by HGNC (HUGO gene nomenclature committee), e.g., Gene ID: 301, sequence available at NCBI. In an embodiment, the annexin A1 is encoded by ANXA1, Gene ID: 301 as listed 18 Mar. 2022 at NCBI.

An antibody is provided which binds annexin A1, or an annexin A1-binding fragment thereof or annexin A1-binding fusion protein, comprising complementary-determining regions CDR1 through CDR6, wherein one or more of CDR1 through CDR6 has 85% or greater identity with, but not 100% identity with, the CDR1 through CDR6 sequences set forth as follows:

```
e)
a heavy chain comprising:
                                      (SEQ ID NO: 2)
CDR1 having the sequence GFTFSDFY;

(SEQ ID NO: 4)
CDR2 having the sequence SKNKANDYTT;

(SEQ ID NO: 6)
CDR3 having the sequence AAGGYDEGVGWYFDV;
and a light chain comprising:
                                      (SEQ ID NO: 8)
CDR4 having the sequence QNVGTN;

(SEQ ID NO: 10)
CDR5 having the sequence SAS;

(SEQ ID NO: 12)
CDR6 having the sequence QQYNNYPYT;
or f)
a heavy chain comprising:
                                      (SEQ ID NO: 14)
CDR1 having the sequence GYTFTNYW;

(SEQ ID NO: 16)
CDR2 having the sequence VYPGGGYI;

(SEQ ID NO: 18)
CDR3 having the sequence ARWGTTVDWYFDV;
and a light chain comprising:
                                      (SEQ ID NO: 20)
CDR4 having the sequence SSVSY;

(SEQ ID NO: 22)
CDR5 having the sequence DTS;

(SEQ ID NO: 24)
CDR6 having the sequence QQWSSNPYT;
or g)
a heavy chain comprising:
                                      (SEQ ID NO: 26)
CDR1 having the sequence GFTFSDYD;

(SEQ ID NO: 28)
CDR2 having the sequence ISDGGSFT;

(SEQ ID NO: 30)
CDR3 having the sequence AKKKGYGDAMDY;
and a light chain comprising:
                                      (SEQ ID NO: 32)
CDR4 having the sequence EDIFIR;

(SEQ ID NO: 34)
CDR5 having the sequence GAT;

(SEQ ID NO: 36)
CDR6 having the sequence QQYWNTPWT.
```

A pharmaceutical composition is provided comprising:

(i) the antibody, annexin A1-binding fragment, or fusion protein, as described herein, and a carrier; or (ii) two different antibodies, annexin A1-binding fragments, or fusion proteins, as described herein, and a carrier.

A method of reducing development of or treating a cancer is provided, comprising administering to a subject having the cancer an amount of an antibody which binds annexin A1, or an annexin A1-binding fragment thereof or fusion protein, as described herein, effective to reduce development of or treat a cancer.

A method of reducing development of and/or treating a Familial Adenomatous Polyposis (FAP) in a subject, comprising administering to a subject having FAP an amount of an antibody which binds annexin A1, or an annexin A1-binding fragment thereof or fusion protein, as described herein, effective to reduce development of or treat FAP.

A method of reducing development of or treating a solid tumor is provided, comprising administering to a subject having the solid tumor an amount of an antibody which binds annexin A1, or an annexin A1-binding fragment thereof or fusion protein, as described herein, effective to reduce development of or treat a solid tumor.

A method of reducing development of or treating a cancer or Familial Adenomatous Polyposis (FAP) is provided, comprising administering to a subject having the cancer an amount of the pharmaceutical composition as described herein effective to reduce development of or treat a cancer or FAP.

In embodiments, the cancer is a colorectal cancer or a pancreatic cancer.

In embodiments, the cancer is a cancer of a liver, lung, bladder, small intestine, or endometrium, or is a melanoma.

In embodiments, the cancer is a pancreatic cancer and a reduction in pancreatic cancer tumor volume is effected by the method.

In embodiments, the antibody, an annexin A1-binding fragment thereof or fusion protein is administered systemically.

In embodiments, the antibody, an annexin A1-binding fragment thereof or fusion protein is administered locally to an affected organ in the subject.

In embodiments, the antibody, an annexin A1-binding fragment thereof or fusion protein is administered directly into a colon of the subject.

In embodiments, the antibody, an annexin A1-binding fragment thereof or fusion protein is administered directly into a pancreas of the subject.

In embodiments, the antibody, an annexin A1-binding fragment thereof or fusion protein is administered subcutaneously, intravenously, or intramuscularly. In embodiments, the antibody, an annexin A1-binding fragment thereof or fusion protein is administered into the colon. In embodiments, the antibody is administered into the tumor or cancer.

In embodiments, the antibody is administered and is a monospecific antibody.

In embodiments, the antibody is administered and is a bispecific antibody.

In embodiments, at least two monospecific anti-annexin A1 antibodies are administered and wherein the two antibodies differ in their heavy chain CDR sequences and/or their light chain CDR sequences.

A method is provided of reducing development of or treating a cancer, comprising administering to a subject having the cancer an amount of two different antibodies which bind annexin A1, or two different annexin A1-binding fragments thereof, or two different fusion proteins, as described herein, or pharmaceutical composition comprising such, effective to reduce development of or treat a cancer.

A method is provided of reducing development of or treating a Familial Adenomatous Polyposis (FAP), comprising administering to a subject having the FAP an amount of two different antibodies which bind annexin A1, or two different annexin A1-binding fragments thereof, or two different fusion proteins, as described herein, or pharmaceutical composition comprising such, effective to reduce development of or treat FAP.

In embodiments, a first antibody (i) comprises a heavy chain and a light chain as set forth in a) hereinabove, and a second antibody (ii) comprises a heavy chain and a light chain as set forth in b) hereinabove. In embodiments, a first antibody (i) comprises a heavy chain and a light chain as set forth in a) hereinabove, and a second antibody (ii) comprises a heavy chain and a light chain as set forth in c) hereinabove. In embodiments, a first antibody (i) comprises a heavy chain and a light chain as set forth in b) hereinabove, and a second antibody (ii) comprises a heavy chain and a light chain as set forth in c) hereinabove.

In embodiments, the methods further comprise receiving identification of the subject, or identifying the subject, as having FAP prior to administration of the treatment.

In embodiments, identification of, or identifying, the subject as having FAP comprises quantifying a level of annexin A1 on proliferating cells of a sample of the subject as in excess of a control level of annexin A1 for a sample.

A method is provided of reducing resistance to a chemotherapy for a cancer in a subject, comprising administering to the subject an amount of an antibody which binds annexin A1, or an annexin A1-binding fragment thereof, or fusion protein, as described herein or pharmaceutical composition as described herein, effective to reduce resistance to a chemotherapy being administered or to be administered to the subject.

In embodiments, the chemotherapy is for a colorectal cancer.

In embodiments, the methods further comprise receiving identification of the subject, or identifying the subject, as suitable for an anti-annexin A1 treatment prior to administration of the treatment.

In embodiments, identification of, or identifying, the subject as having FAP comprises quantifying a level of annexin A1 on proliferating cells of a sample of the subject as in excess of a control level of annexin A1 for a sample.

A nucleic acid is provided encoding a heavy chain as described herein.

A nucleic acid is provided encoding a light chain as described herein.

In embodiments, the nucleic acid is an expression vector.

A hybridoma is provided comprising a nucleic acid as described herein. A host cell is provided comprising a nucleic acid as described herein. In embodiments, the host cell is a mammalian cell. In embodiments, the host cell is derived from a mammalian cell. In embodiments, the host cell is a CHO, NS0, Sp2/0, HEK293, or PER.C6 cell.

An antibody is provided which binds annexin A1, or an annexin A1-binding fragment thereof, or a fusion protein, as described herein, for use as a medicament in treating a cancer or FAP or for reducing resistance to a chemotherapy.

A combination of two or more different antibodies which bind annexin A1, or two or more different annexin A1-binding fragments thereof, or two or more different fusion proteins, as described herein, for use as a medicament in treating a cancer or FAP.

In embodiments, the anti-annexin A1 antibody or fragment thereof, comprises (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02. In embodiments, the anti-annexin A1 antibody or fragment thereof, comprises an optimized version of, having less than 100% sequence identity with, a (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02.

Fragments of antibodies can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In embodiments, a linker of the scFv is 10-25 amino acids in length. In an embodiment the peptide linker comprises glycine, serine and/or threonine residues. (For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain can be in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety).

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In contrast to polyclonal antibody preparations, which typically include different antibodies directed against different determinants (epitopes), each monoclonal antibody of a monospecific monoclonal antibody preparation is directed against a single determinant on an antigen. A bispecific antibody, recognizing two antigens, in one embodiment, can be manufactured from two monoclonal antibodies. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature absent the hand of man.

In an embodiment the antibody is humanized. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDR1-3 of both the heavy and light chain of the antibodies described herein. In a preferred embodiment, framework (FR) residues of the murine mAb are replaced with corresponding human immunoglobulin variable domain framework (FR) residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are well known. Some are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more, or all, CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

The term "$K_d$", as used herein, is intended to refer to the dissociation constant of an antibody-antigen interaction. One way of determining the $K_d$ or binding affinity of antibodies to the annexin A1 can be by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used. For example, ELISA.

In embodiments, the antibody or antigen-binding fragment thereof or fusion protein binds to a human annexin A1 with an affinity of 100.0 nM KD or stronger.

In embodiments, the antibody or antigen-binding fragment thereof or fusion protein binds to a human annexin A1 with an affinity of 10.0 nM $K_D$ or stronger.

In embodiments, the antibody or antigen-binding fragment thereof or fusion protein binds to a human annexin A1 with an affinity of 2.0 nM $K_D$ or stronger.

In embodiments, the antibody or antigen-binding fragment thereof or fusion protein binds to a human annexin A1 with an affinity of 1.0 nM $K_D$ or stronger.

In embodiments, the antibodies of the invention have an $EC_{50}$ for the antigen annexin A1 of 100 ng/ml or less.

An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a given sequence in annexin A1 is an antibody that binds this epitope with greater affinity, avidity, more readily, and/or with greater duration than it binds to other epitopes. In embodiments of the antibodies or fragments, herein the antibodies or fragments preferentially bind human annexin A1. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)

hereby incorporated by reference in its entirety). There are CDRs 1, 2, and 3 for each of the heavy and light chains. Chothia refers instead to the location of the structural loops (Chothia and Lesk, J. Mol. Biol. 196:901-917 (1987)). The AbM HVRs represent a compromise between the Kabat HVRs and Chothia structural loops and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

In embodiments, the variable regions disclosed herein are not modified. In embodiments, the invention encompasses modifications to the variable regions disclosed herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to human annexin A1. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

A modification or mutation may also be made in a framework region or constant region to increase the half-life of an antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the fusion protein is produced in a eukaryotic expression system.

In an embodiment, the fusion protein produced in the eukaryotic expression system comprises glycosylation at a residue on the Fc portion corresponding to Asn297.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and a naphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

Administration can be auricular, buccal, conjunctival, cutaneous, subcutaneous, endocervical, endosinusial, endotracheal, enteral, epidural, via hemodialysis, interstitial, intraabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjunctival, sublingual, submucosal, topically, transdermal, transmucosal, transplacental, transtracheal, ureteral, uretheral, and vaginal.

In embodiments, the antibody, fragment or fusion protein is administered at a dose of 0.5 mg/kg to 100 mg/kg. In embodiments, the antibody, fragment or fusion protein is administered at a dose of 101 mg/kg to 250 mg/kg. In embodiments, the antibody, fragment or fusion protein is administered at a dose of 251 mg/kg to 500 mg/kg. In embodiments, the antibody, fragment or fusion protein is administered at a dose of 501 mg/kg to 1000 mg/kg. In embodiments, the antibody, fragment or fusion protein is administered at a dose of 1001 mg/kg to 2000 mg/kg. In embodiments, the antibody, fragment or fusion protein is administered at a dose of up to 25 mg twice per daily, daily, every other day, weekly, monthly or every three months. In embodiments, the antibody, fragment or fusion protein is administered at a dose of 25 to 100 mg twice per daily, daily, every other day, weekly, monthly or every three months. In embodiments, the antibody, fragment or fusion protein is administered at a dose of 100 to 250 mg twice per daily, daily, every other day, weekly, monthly or every three months. In embodiments, the antibody, fragment or fusion protein is administered at a dose of 250 to 500 mg twice per daily, daily, every other day, weekly, monthly or every three months. In embodiments, the antibody, fragment or fusion protein is administered at a dose of 500 to 1000 mg twice per daily, daily, every other day, weekly, monthly or every three months. In embodiments, the antibody, fragment or fusion protein is administered at a dose of 1000 to 2000 mg twice per daily, daily, every other day, weekly, monthly or every three months.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means a mammal. Mammals include canines, felines, rodents, bovine, equines, porcines, ovines, and primates including humans. Thus, the invention can be used in human medicine or also in veterinary medicine, e.g., to treat companion animals, farm animals, laboratory animals in zoological parks, and animals in the wild. The invention is particularly desirable for human medical applications. In a preferred embodiment the subject is a human.

The term "patient" as used in this application means a human subject. In some embodiments of the present invention, the "patient" is one suffering with cancer, such as colorectal cancer, or FAP.

The terms "treat", "treatment" of a disease, and the like refer to slowing down, relieving, ameliorating or alleviating at least one of the symptoms of the disease, or reversing the disease after its onset, preventing or reducing tumor growth, reducing tumor size, preventing or slowing the spread of metastasis, reversing (at least partially) chemo-resistance, and any other subjective or objective improvement in the patient related to the patient's cancer.

The terms "prevent", "prevention", and the like refer to acting prior to overt disease or disorder onset, to prevent the disease or disorder from developing or minimize the extent of the disease or disorder or slow its course of development.

The term "in need thereof" with regard to a subject would be a subject known or suspected of having or being at risk of developing cancer, in particular, colorectal cancer.

A subject in need of treatment would be one that has already developed the disease or disorder. A subject in need of prevention would be one with risk factors of cancer, in particular colorectal cancer, including having FAP or a high level of Annexin A1 in the colorectal tissue indicating high risk of occurrence The terms "therapeutically effective amount" or "amount effective to" encompasses an amount sufficient to ameliorate or prevent a symptom or sign of the medical condition. Effective amount also means an amount sufficient to allow or facilitate diagnosis. An effective amount for a particular subject may vary depending on factors such as the condition being treated, the overall health of the patient, the method route and dose of administration and the severity of side effects. An effective amount can be the maximal dose or dosing protocol that avoids significant side effects or toxic effects.

The terms "cancer", "tumor", "cancerous", and "malignant" refer to or describe the well-known physiological condition in mammals that is typically characterized by unregulated cell growth.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

In embodiments, the antibodies or fragments as described herein, with or without detectable marker(s), can be used to quantify or measure the level of annexin A1 in a sample or tissue as employed in methods herein described.

EXPERIMENTAL RESULTS

Annexin A1 belongs to the Annexin family of Ca2+-dependent phospholipid-binding proteins, with a molecular weight of 35-40 KD, and is present in both cytoplasma and membrane. Annexin A1 has been suggested to play a role in resolution of inflammation (Peretti et al. 2009). Annexin A1 has been postulated to be either a tumor suppressor or promoter depending on tumor type (Guo et al. 2013; Boudhraa et al. 2016). Although annexin A1 has been associated with CRC (Onozawa et al. 2017; Su et al. 2010), its actual role in CRC was unclear.

Disclosed herein are three monoclonal antibodies (mAbs) raised against human annexin A1 which effectively inhibit tumor growth both in vitro and in xenograft mouse models.

mAb 2C1 has the following composition:

|  |  | Nucleotide Sequence | Amino Acid Sequence |
|---|---|---|---|
| Heavy Chain | CDR1 | gggttcaccttcagtgatttcta t (SEQ ID NO: 1) | GFTFSDFY (SEQ ID NO: 2) |
|  | CDR2 | agtaaaaacaaagctaatgatta tacaaca (SEQ ID NO: 3) | SKNKANDYTT (SEQ ID NO: 4) |
|  | CDR3 | gccgctgggggttacgacgaggg agttggctggtacttcgatgtc (SEQ ID NO: 5) | AAGGYDEGVGWYFDV (SEQ ID NO: 6) |
| Light Chain | CDR1 | cagaatgtgggtactaat (SEQ ID NO: 7) | QNVGTN (SEQ ID NO: 8) |
|  | CDR2 | tcggcatcc (SEQ ID NO: 9) | SAS (SEQ ID NO: 10) |
|  | CDR3 | cagcaatataataactatccgta cacg (SEQ ID. NO: 11) | QQYNNYPYT (SEQ ID NO: 12) |

A diagram of the heavy and light chains for mAB 2C1 is found in FIG. 1.

mAb 3G4 has the following composition:

|  |  | Nucleotide Sequence | Amino Acid Sequence |
|---|---|---|---|
| Heavy Chain | CDR1 | ggctacaccttcactaactact gg (SEQ ID NO: 13) | GYTFTNYW (SEQ ID NO: 14) |
|  | CDR2 | gtttaccctggaggtggttata tt (SEQ ID NO: 15) | VYPGGGYI (SEQ ID NO: 16) |
|  | CDR3 | gcaagatgggggactacggtcg actggtacttcgatgtc (SEQ ID NO: 17) | ARWGTTVDWYFDV (SEQ ID NO: 18) |
| Light Chain | CDR1 | tcaagtgtaagttac (SEQ ID NO: 19) | SSVSY (SEQ ID NO: 20) |
|  | CDR2 | gacacatcc (SEQ ID NO: 21) | DTS (SEQ ID NO: 22) |
|  | CDR3 | cagcagtggagtagtaaccat acacg (SEQ ID. NO: 23) | QQWSSNPYT (SEQ ID NO: 24) |

Figure 2:
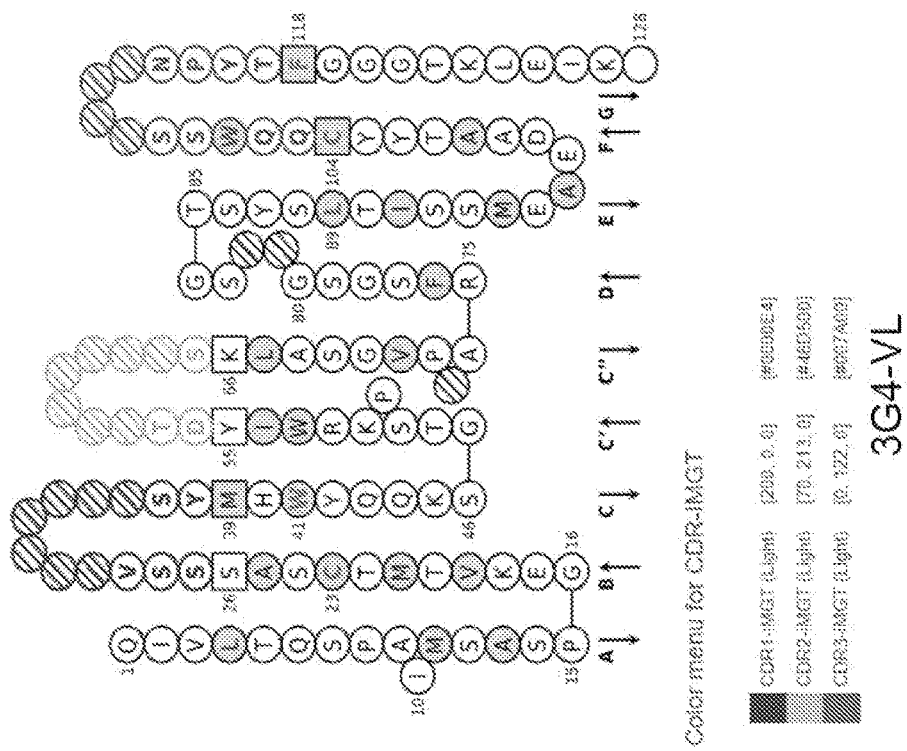
FIG. 2: Diagram of mAb 3G4 sequences (VH SEQ ID NO:39; VL SEQ ID NO:40). Diagonally marked residues in CDRs absent, shown for structural convenience.
Figure 2:
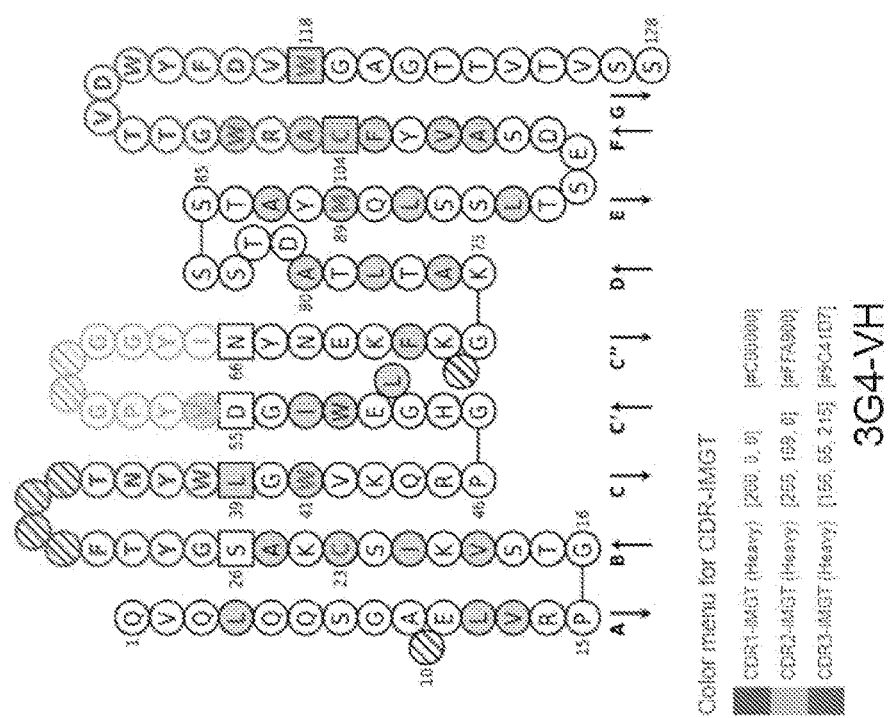

A diagram of the heavy and light chains for mAB 3G4 is found in FIG. 2.

mAb 3D6 has the following composition:

|  |  | Nucleotide Sequence | Amino Acid Sequence |
|---|---|---|---|
| Heavy Chain | CDR1 | ggattcactttcagtgactatg ac (SEQ ID NO: 25) | GFTFSDYD (SEQ ID NO: 26) |
|  | CDR2 | attagtgatggtggtagttttca cc (SEQ ID NO: 27) | ISDGGSFT (SEQ ID NO: 28) |
|  | CDR3 | gcaaaaaagaagggctatggtg atgctatggactac (SEQ ID NO: 29) | AKKKGYGDAMDY (SEQ ID NO: 30) |
| Light Chain | CDR1 | gaggacatttttattcgg (SEQ ID NO: 31) | EDIFIR (SEQ ID NO: 32) |
|  | CDR2 | ggtgcaacc (SEQ ID NO: 33) | GAT (SEQ ID NO: 34) |
|  | CDR3 | caacagtattggaatactccgt ggacg (SEQ ID. NO: 35) | QQYWNTPWT (SEQ ID NO: 36) |

Figure 3:
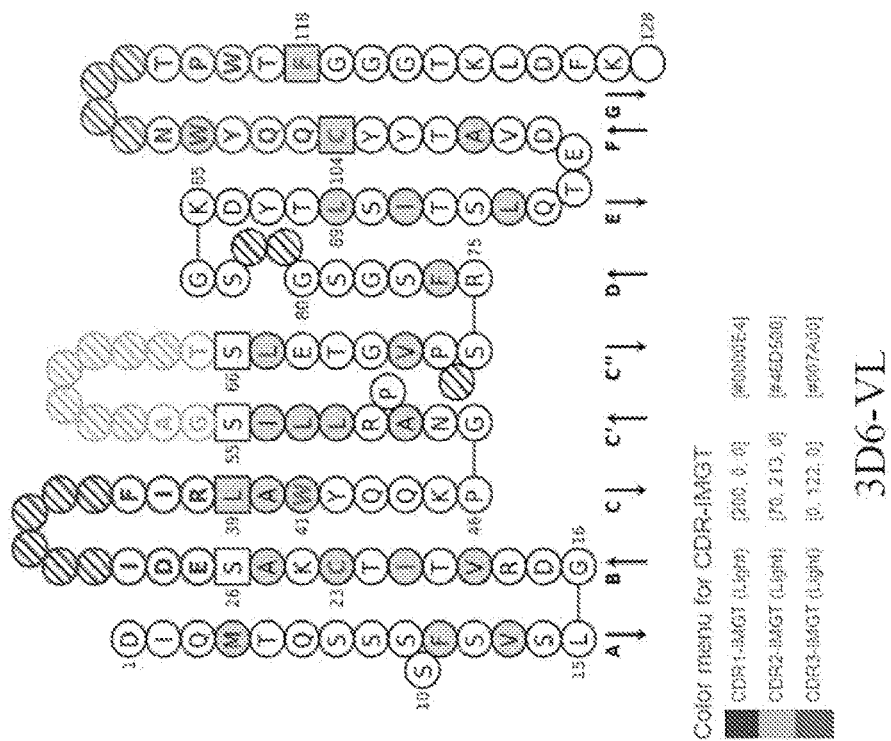
FIG. 3: Diagram of mAb 3D6 sequences (VH SEQ ID NO:41; VL SEQ ID NO:42). Diagonally marked residues in CDRs absent, shown for structural convenience.
Figure 3:
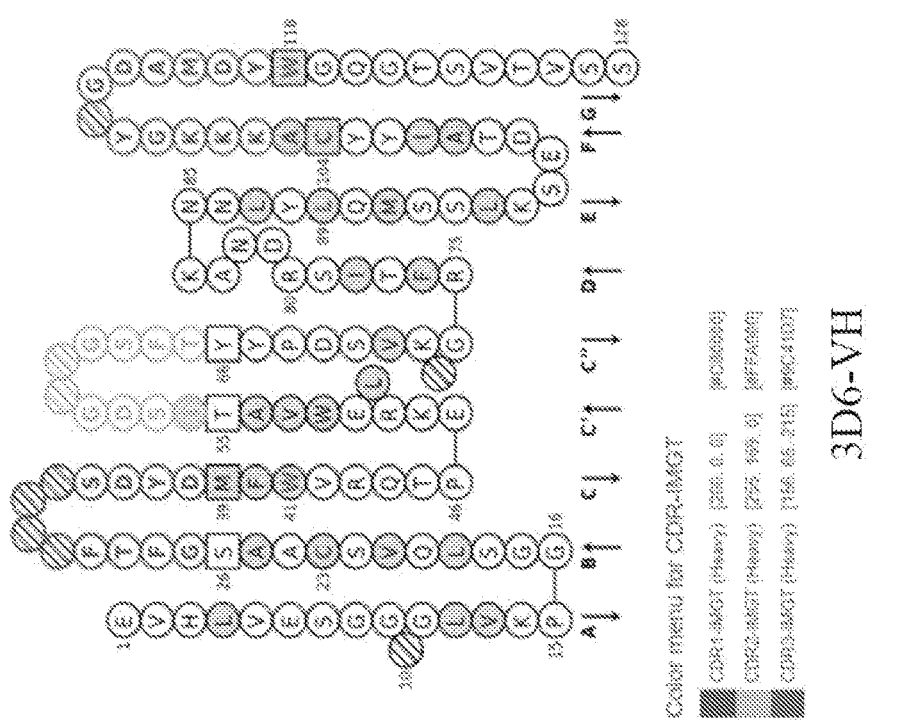

A diagram of the heavy and light chains for mAB 3D6 is found in FIG. 3.

Method: An inoculum of 5×10⁶ HCT116 or MiaPaCa2 cells were injected subcutaneously and bilaterally into 4-5 week old nude mice (mAb 2C1, n=4 for HCT116 and n=3 for MiaPaCa2; mAb 3G4, n=6; mAb 3D6, n=5). Three days later (Day 0), the tumor sizes were measured and designated as 100%. Starting Day 0, an aliquot of 10 μl of 2.5 mg/ml mAb or mouse IgG1 control were injected into the tumors on opposite sides every other day. The tumor sizes were measured daily and expressed in relation to that of Day 0. The differences between tumor sizes of mAb-treated and control groups were assessed using t-test. $*p<0.05$, $**p<0.01$.

Figure 4:
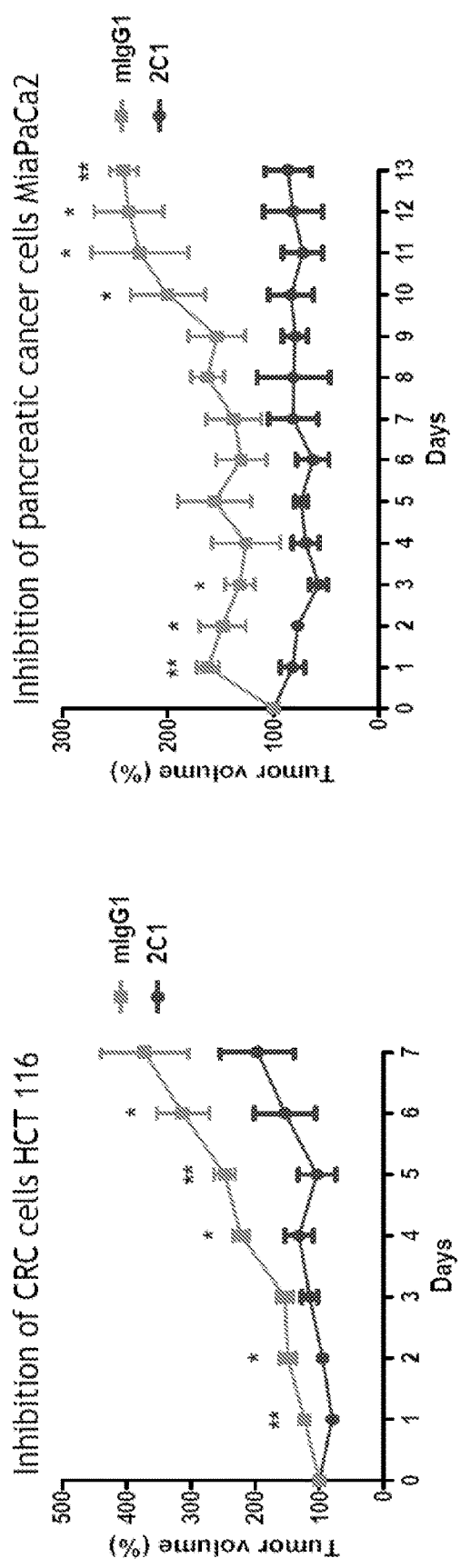
FIG. 4: Graph of the results of the administration of mAb 2C1 to a xenograft mouse model.
Figure 5:
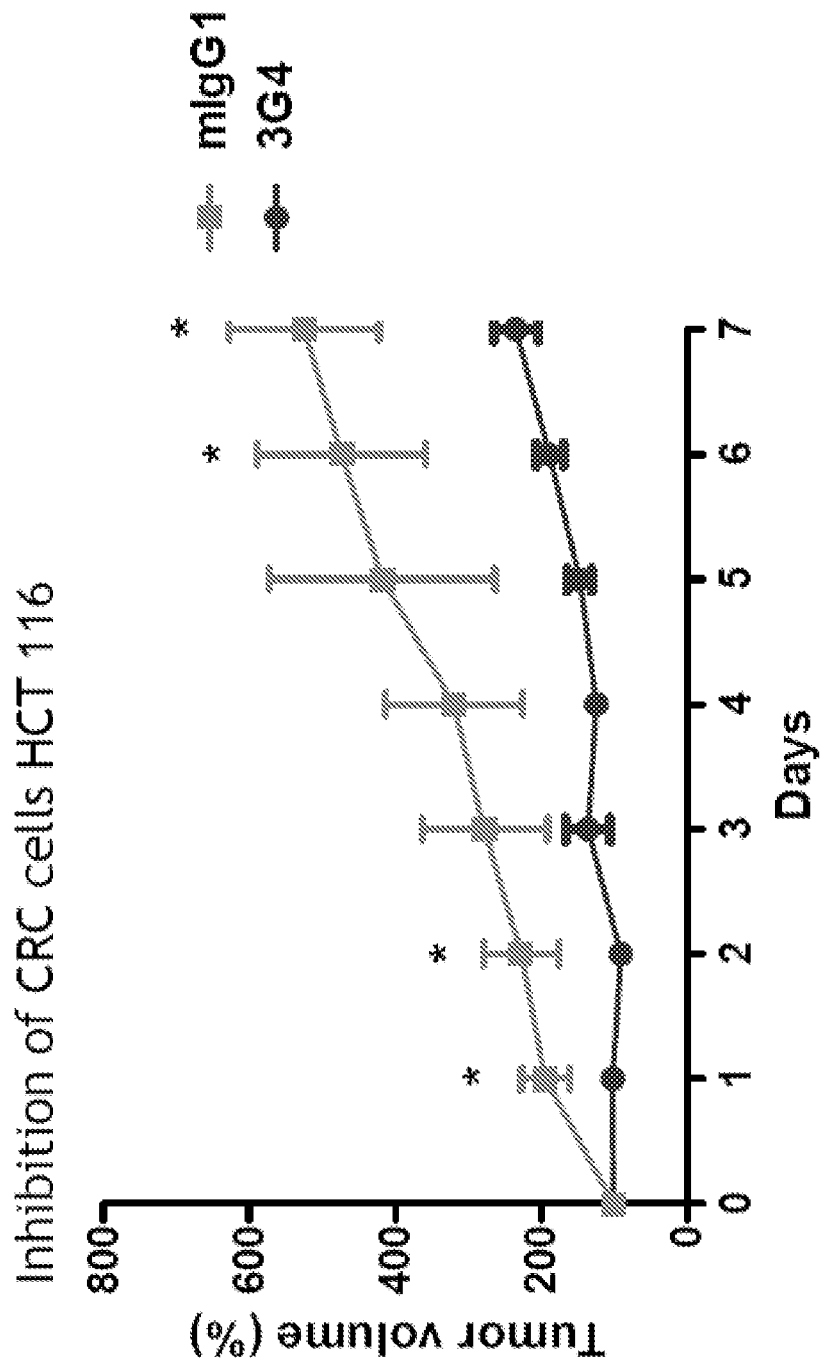
FIG. 5: Graph of the results of the administration of mAb 3G4 to a xenograft mouse model.
Figure 6:
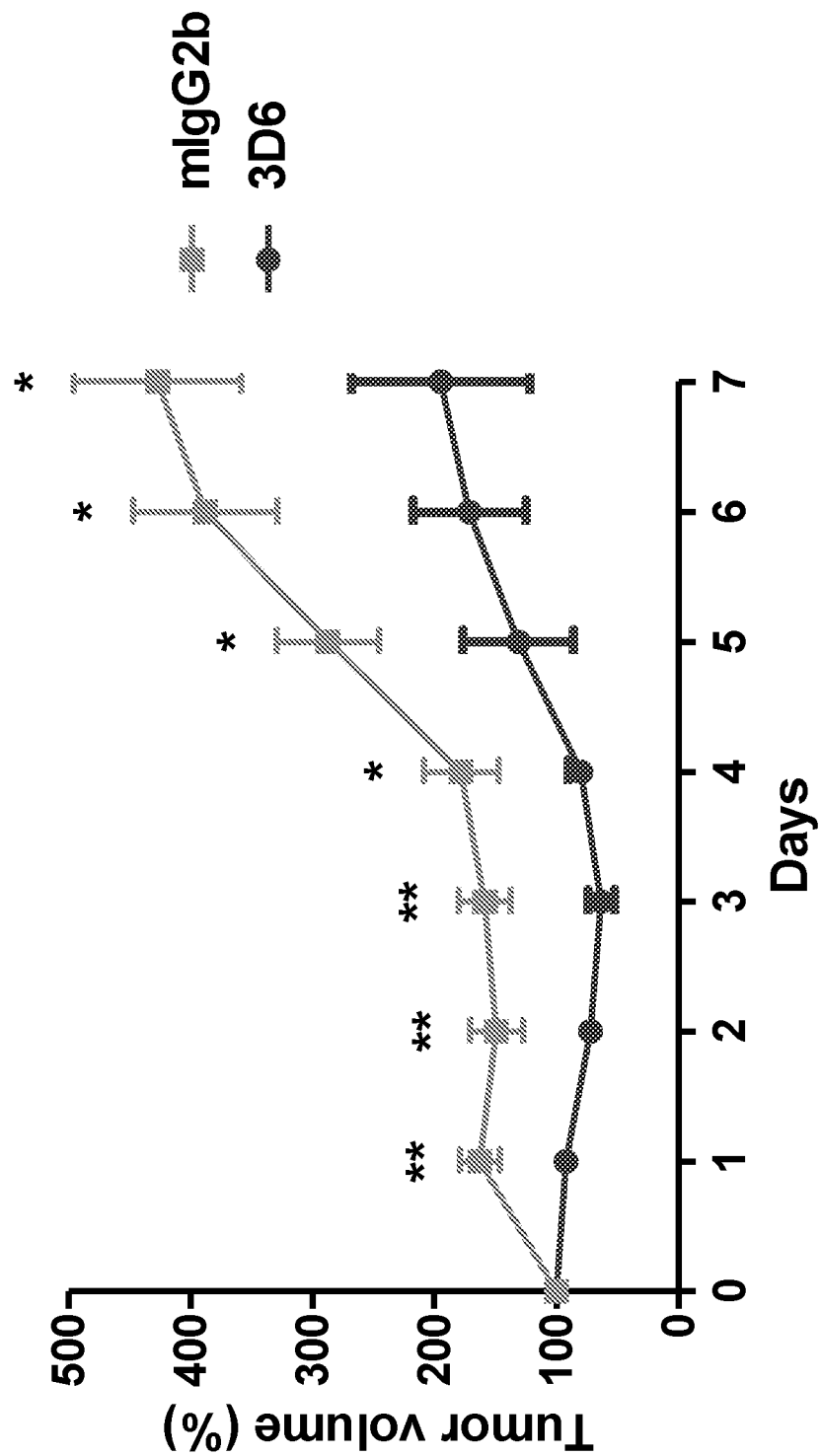
FIG. 6: Graph of the results of the administration of mAb 3D6 to a xenograft mouse model. HCT116 cells.

Results: Results are shown for each mAB. FIG. 4 shows mAB 2C1; FIG. 5 shows mAb 3G4; and FIG. 6 shows mAb 3D6. In each case the mAb inhibited the cancer growth in the xenograft mouse models. mAb 2C1 inhibited both colorectal and pancreatic cancer growth. mAb 3G4 and mAb 3D6 inhibited colorectal cancer growth.

Figures 7A, 7B:
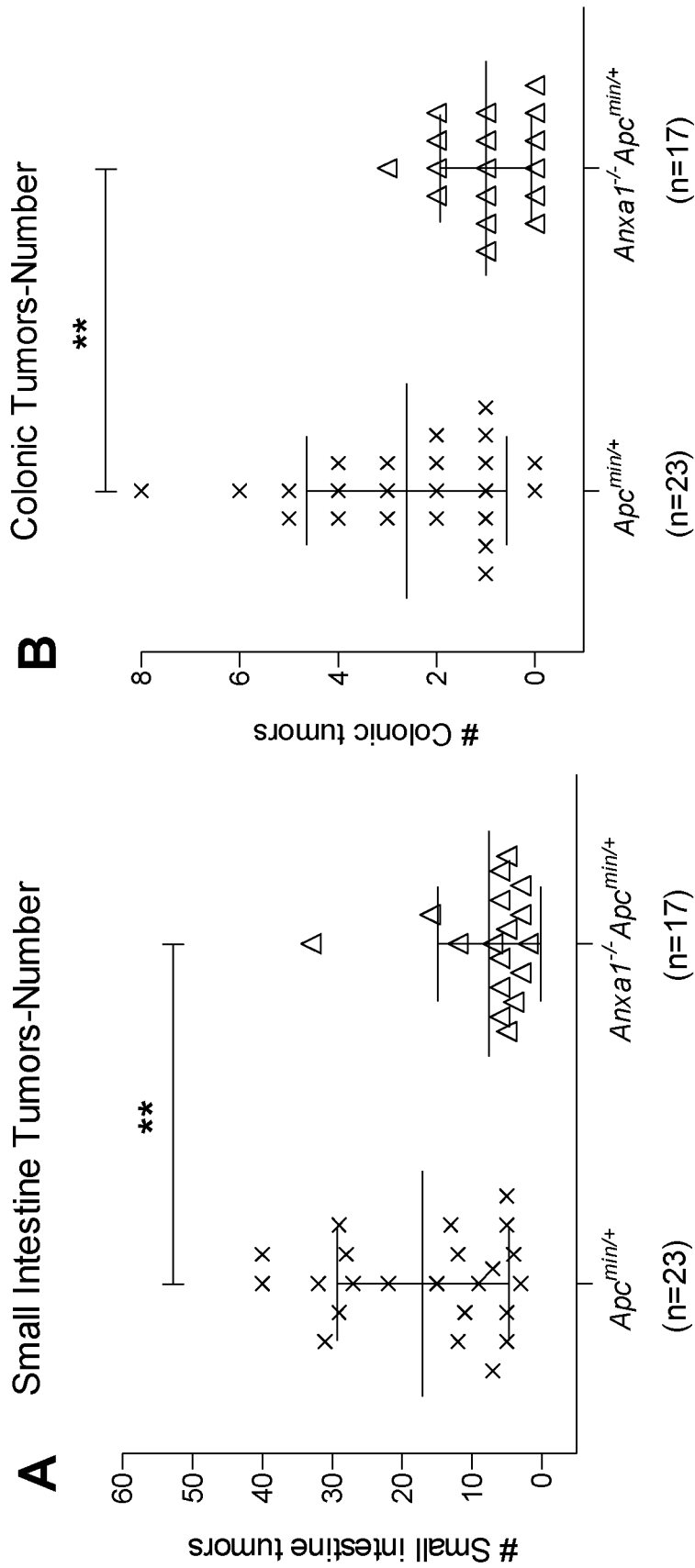
FIGS. 7A-7C: Deletion of ANXA1 prolongs lifespan of $Apc^{min/+}$ animals; 7A: small intestine tumor numbers; 7B: colonic tumor numbers; 7C: percent survival.
Figure 7C:
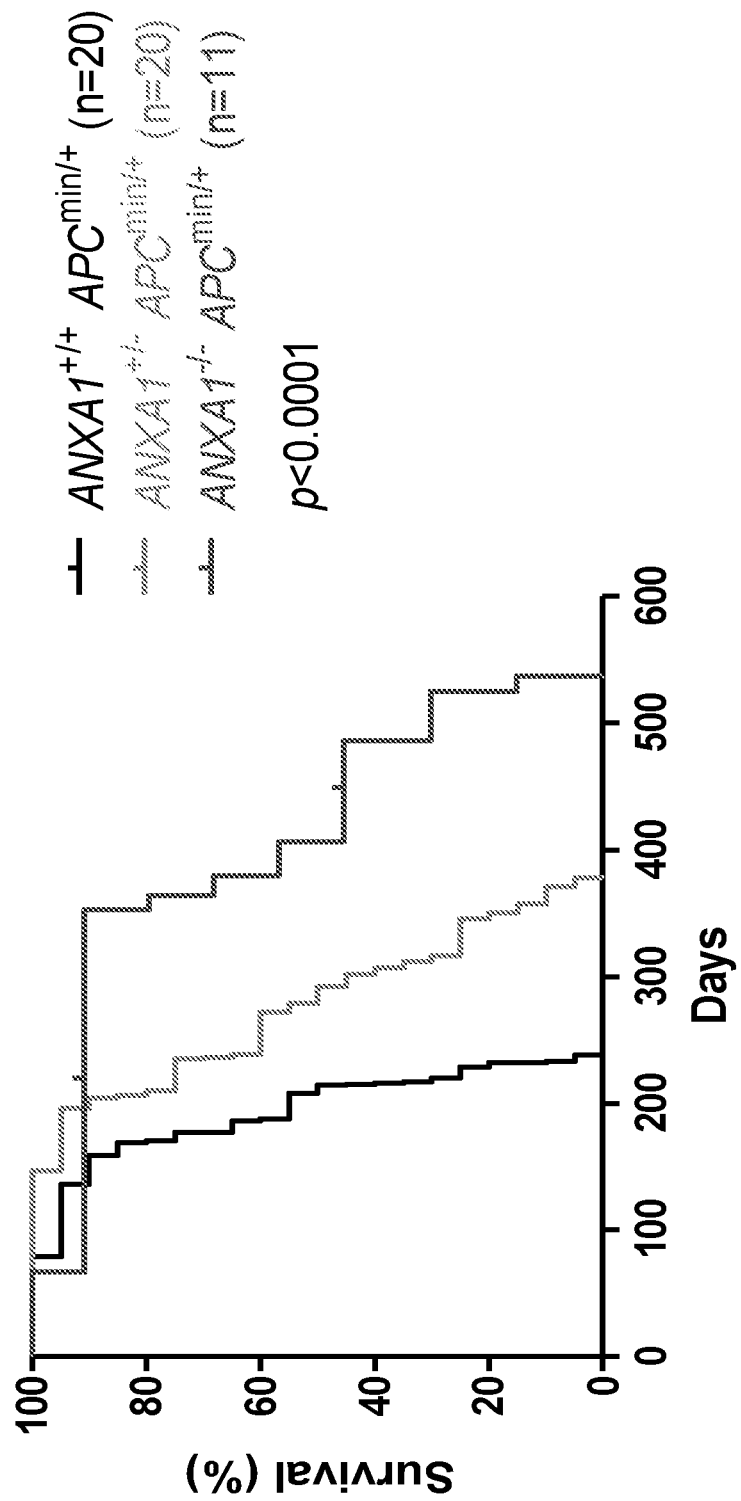

FIGS. 7A-7C show deletion of ANXA1 prolongs lifespan of $Apc^{min/+}$ animals; 7A: small intestine tumor numbers; 7B: colonic tumor numbers; 7C: percent survival.

Figure 8:
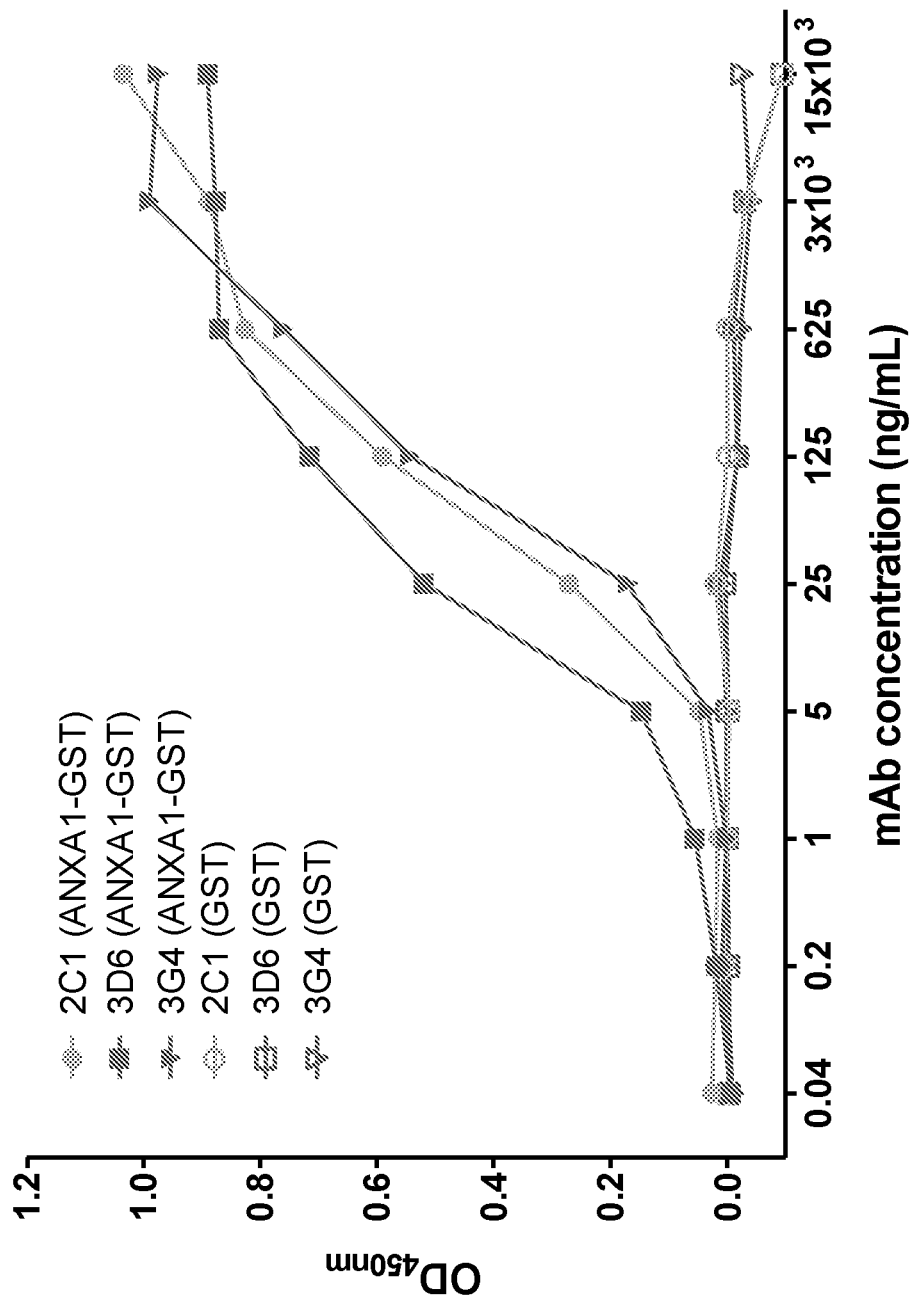
FIG. 8: As measured by ELISA, the half maximal effective concentrations ($EC_{50}$) of the various antibodies disclosed herein are <100 ng/ml, in comparable range as the anti-PD-1 nivolumab and pembrolizumab, which are 76.17 ng/ml (95% CI 64.95-89.34 ng/ml) and 39.90 ng/ml (34.01-46.80 ng/ml), respectively.
Figures 9A, 9B, 9C, 9D:
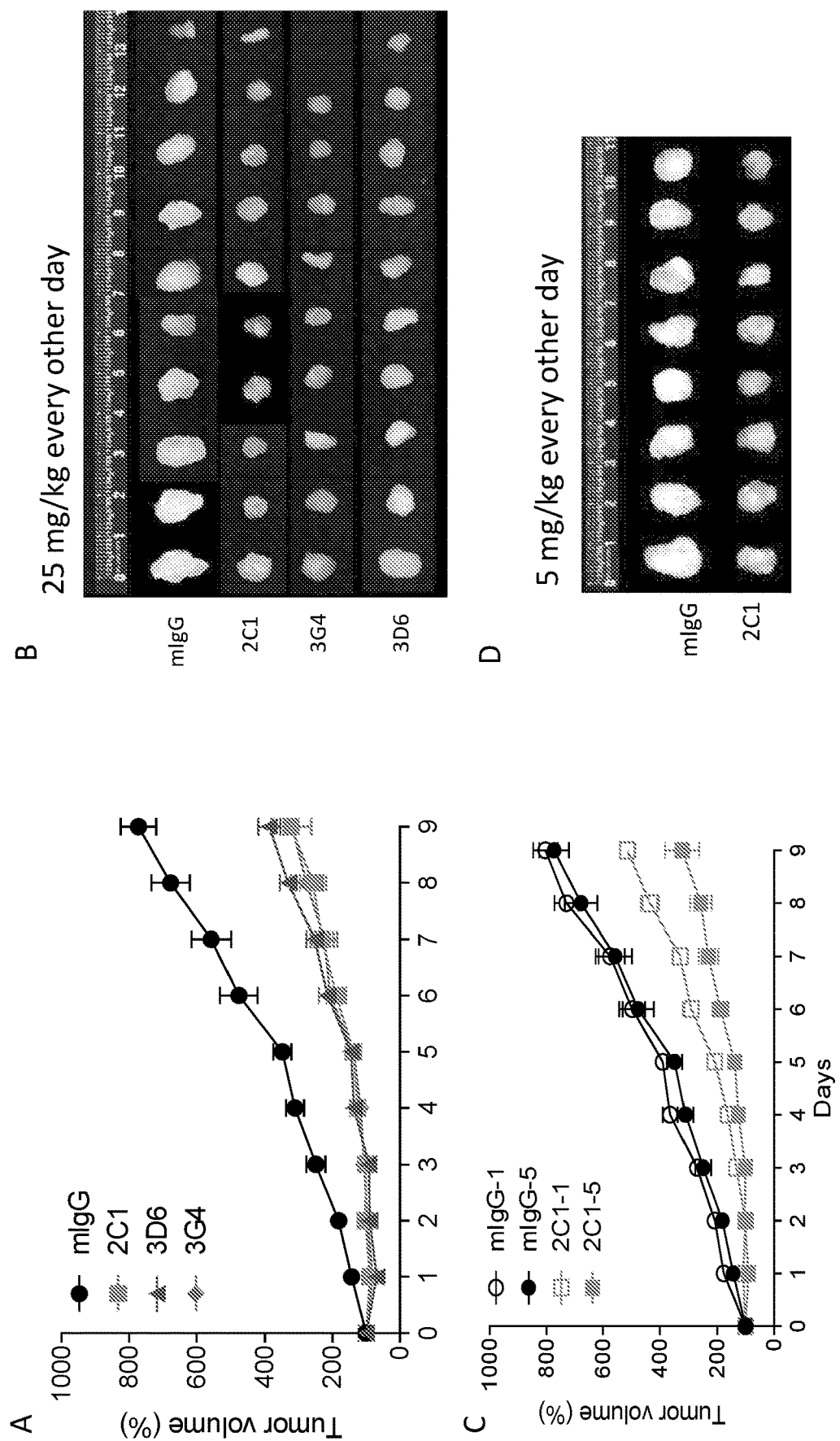
FIGS. 9A-9D: Efficacy of mAb in xenograft model (i.p. injection) for various antibodies as listed. 9A: tumor volume over time for various listed antibodies at 9B 25 mg/kg every other day. 9C: tumor volume over time for various listed antibodies at 9D 5 mg/kg every other day.

FIG. 8 shows that, as measured by ELISA, the half maximal effective concentrations ($EC_{50}$) of the various antibodies are <100 ng/ml, in comparable range as the anti-PD-1 nivolumab and pembrolizumab, which are 76.17 ng/ml (95% CI 64.95-89.34 ng/ml) and 39.90 ng/ml (34.01-46.80 ng/ml), respectively.

FIGS. 9A-9D show the efficacy of the mAbs in xenograft model (i.p. injection) for various antibodies as listed. 9A: tumor volume over time for various listed antibodies at 9B 25 mg/kg every other day. 9C: tumor volume over time for various listed antibodies at 9D 5 mg/kg every other day.

Figure 10:
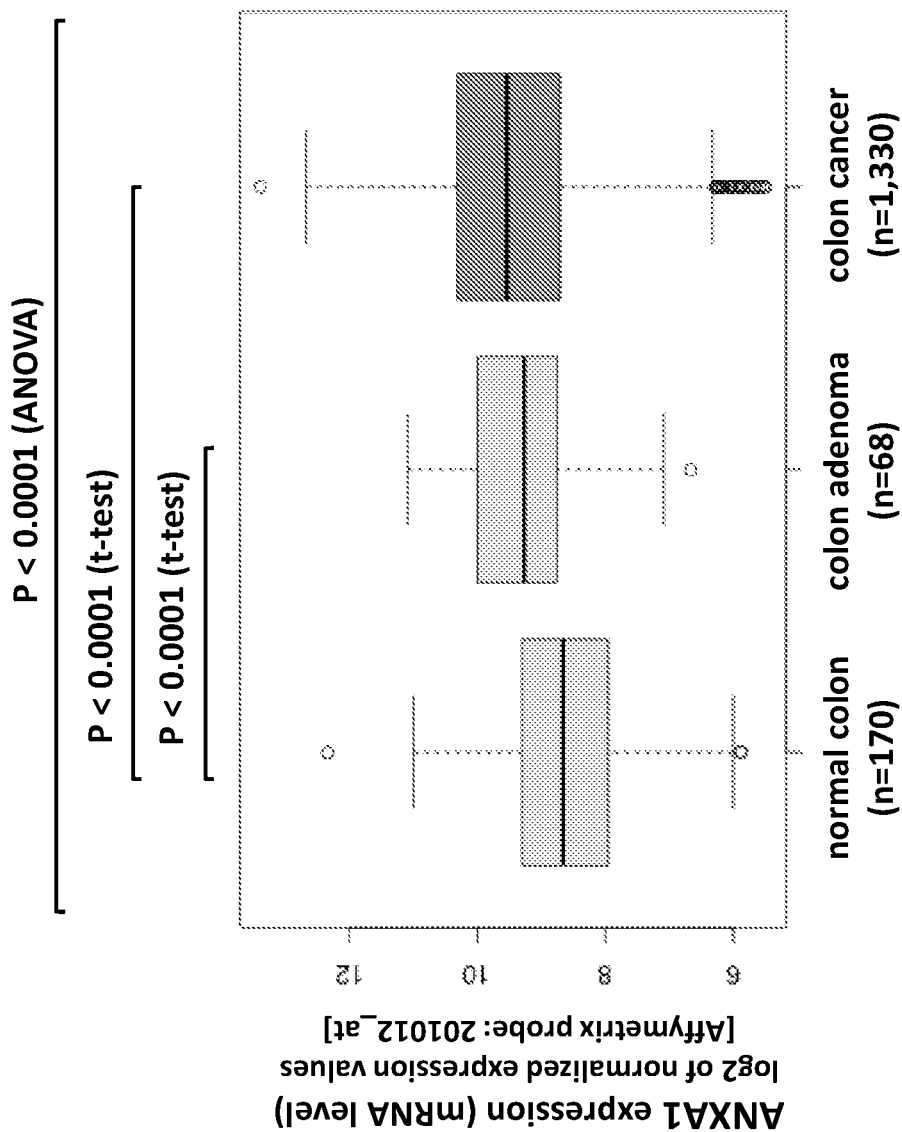
FIG. 10: ANXA1 expression levels (mRNA) increase as normal human colon tissues undergo neoplastic transformation into adenomas and carcinomas. This is confirmed by immunofluorescent staining which showed ANXA1 protein is detected in adenoma tissues but not in adjacent normal tissues.
Figures 11A, 11B:
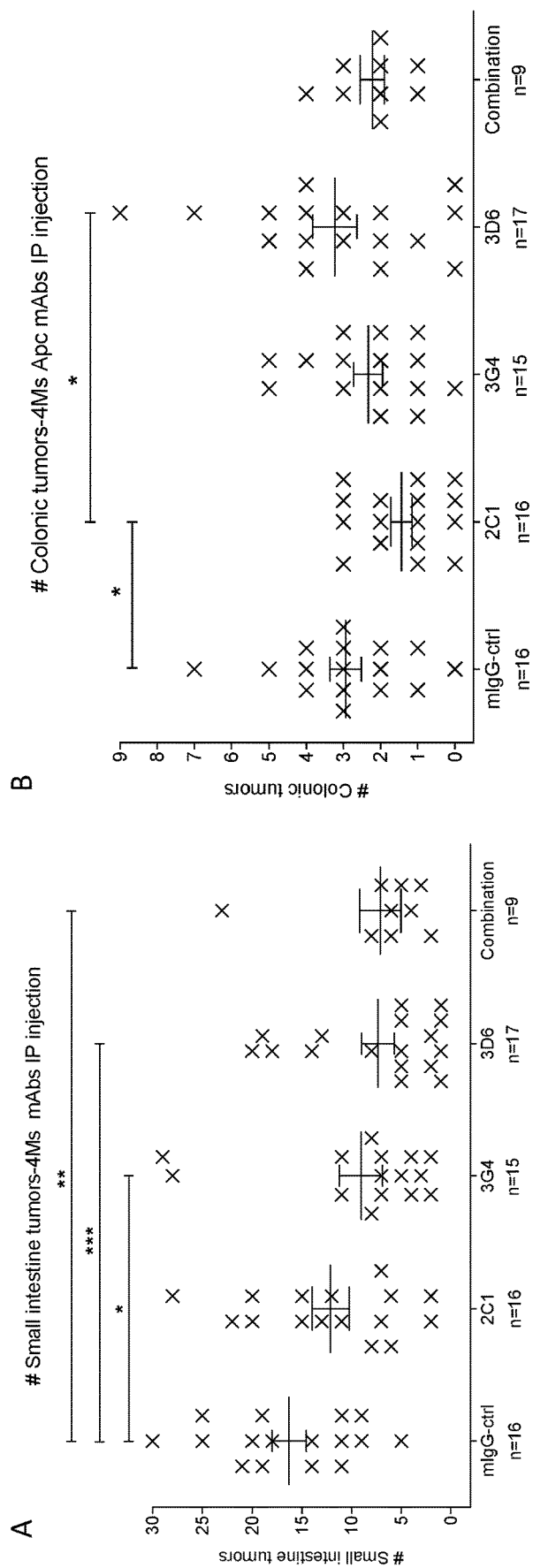
FIGS. 11A-11C: Efficacy of mAbs in $Apc^{min/+}$ model (i.p. injection). 11A: Effect of mAbs on small intestine tumors including combination mAb treatment. 11B: Effect of mAbs on colonic tumors including combination mAb treatment. 11C: Effect of mAbs on volume of tumors for various listed antibody treatments including combination antibodies treatment.
Figure 11C:
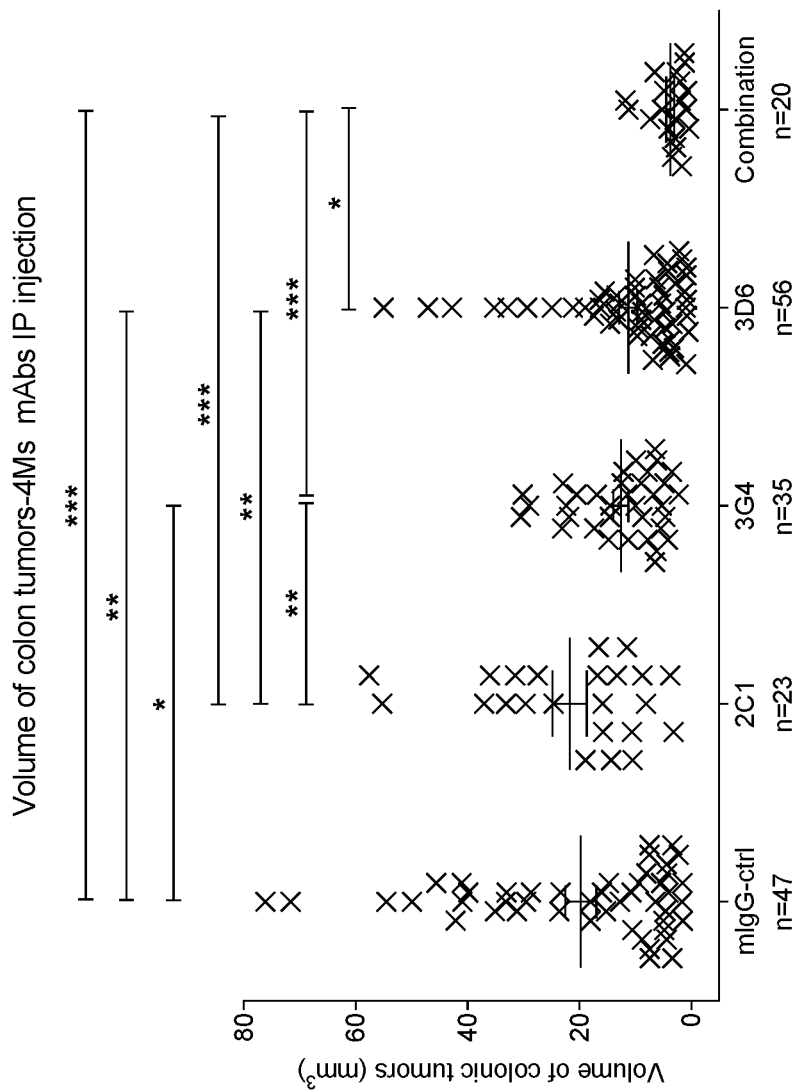

FIG. 10 shows ANXA1 expression levels (mRNA) increase as normal human colon tissues undergo neoplastic transformation into adenomas and carcinomas. This is confirmed by immunofluorescent staining which showed ANXA1 protein is detected in adenoma tissues but not in adjacent normal tissues. FIGS. 11A-11C show the efficacy of the mAbs in $Apc^{min/+}$ model (i.p. injection). 11A: Small intestine tumors including combination mAb treatment. 11B: Colonic tumors including combination mAb treatment. 11C: Volume of tumors for various listed antibody treatments including combination antibodies treatment.

Figure 12:
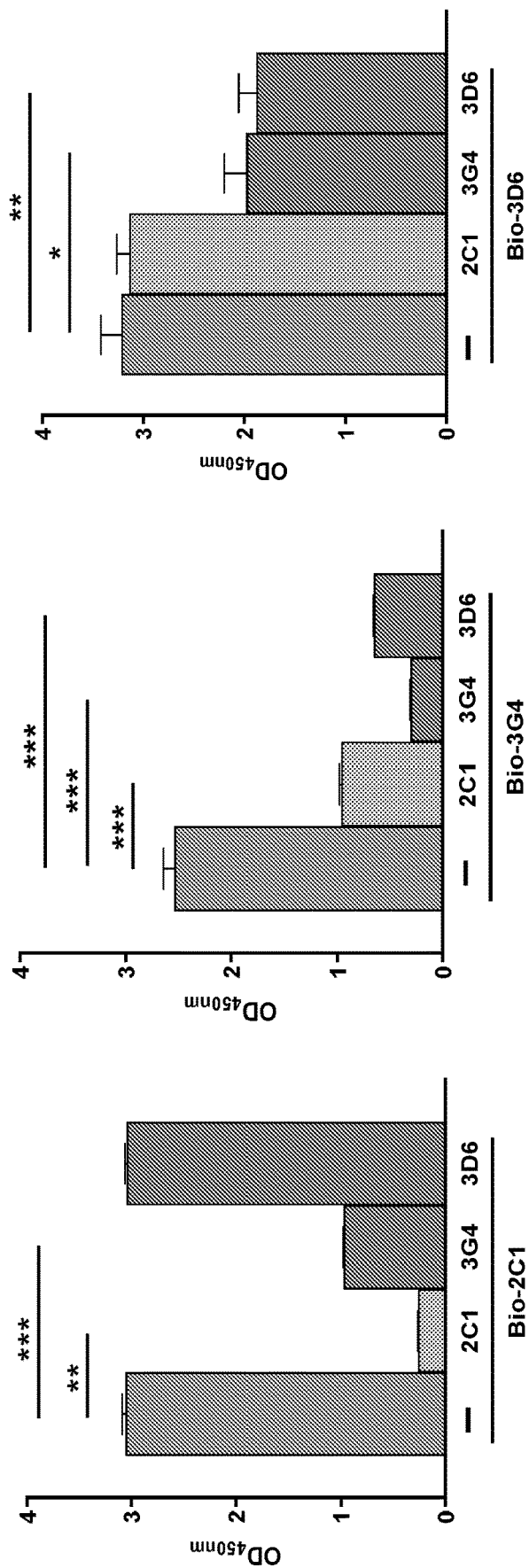
FIG. 12: Using biotinylated mAbs to compete with each non-biotinylated mAb in ELISA, these three plots show that 2C1 and 3D6 recognize different epitopes.

FIG. 12 shows that 2C1 and 3D6 recognize different epitopes of annexin A1.

Figures 13A, 13B:
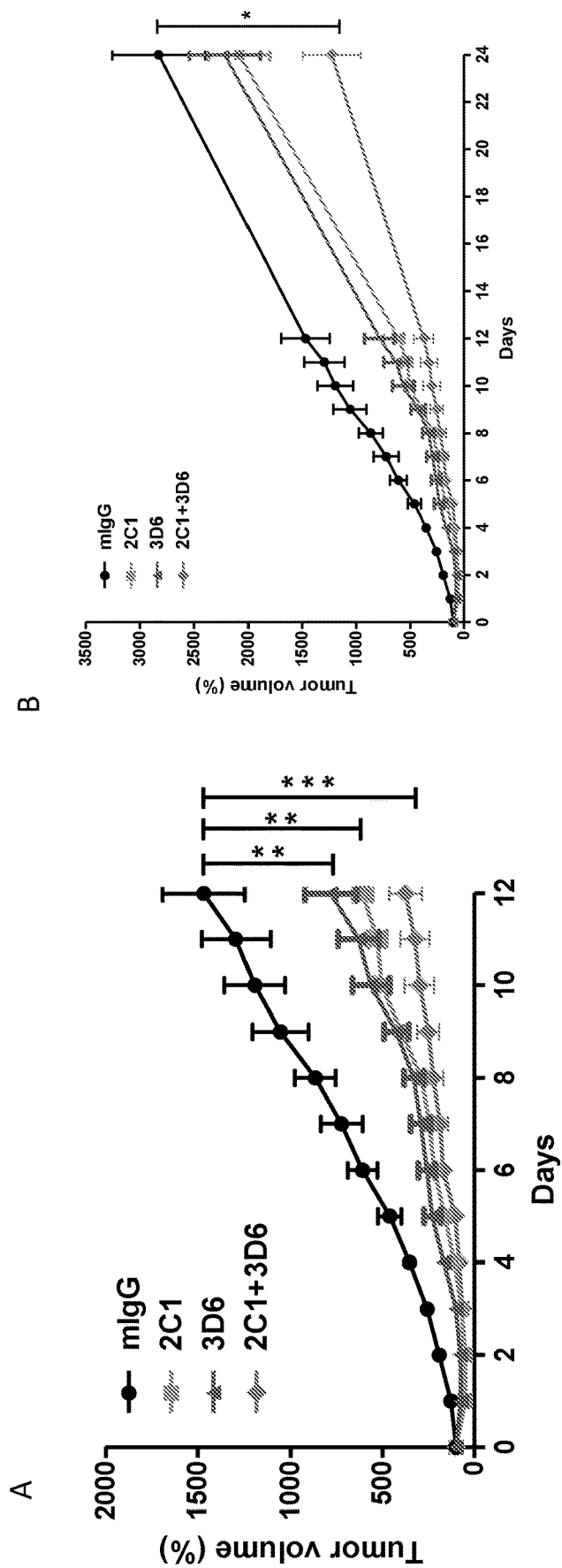
FIGS. 13A-13B: Effects of combination of 2C1 and 3D6 in CDX (cell line). 13A: 0-12 days. 13B: 0-24 days. HCT116 cells.

FIGS. 13A-13B show the effects of 2C1 and 3D6 combination in CDX. 13A: 0-12 days. 13B: 0-24 days.

Figure 14:
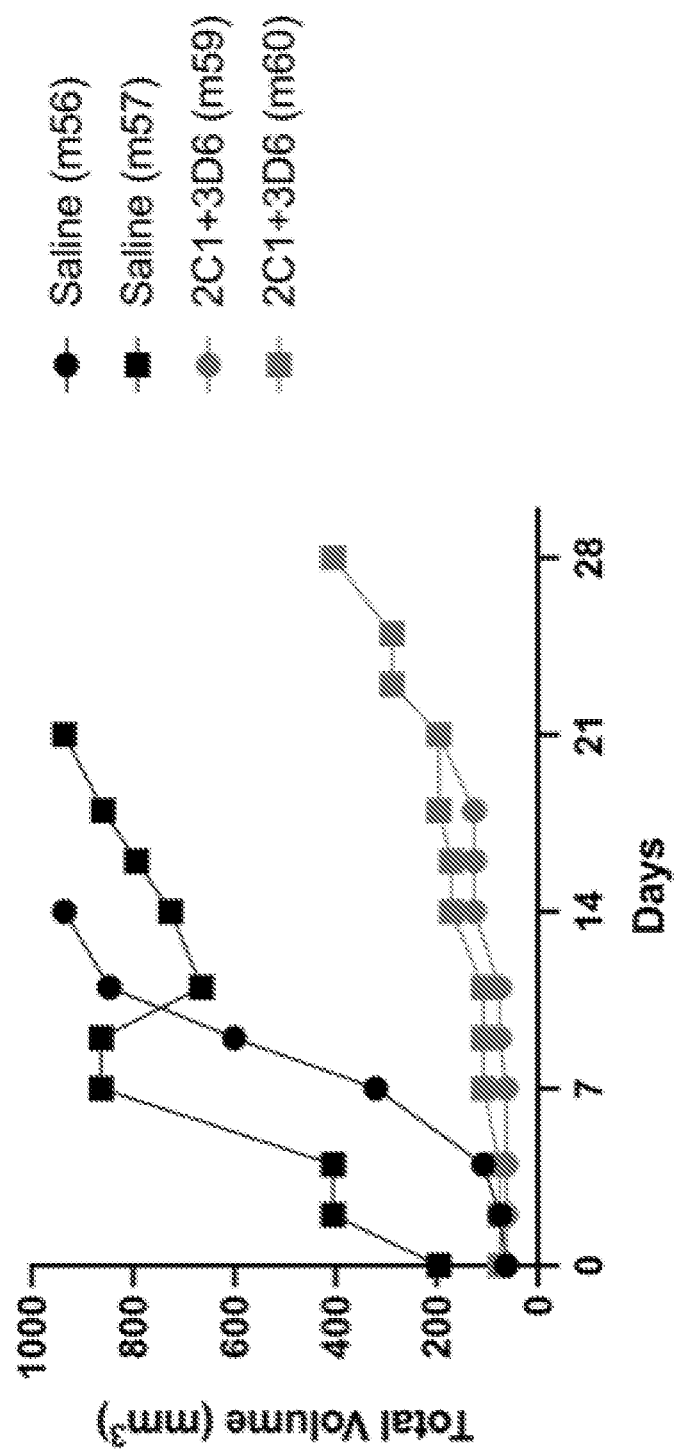
FIG. 14: Effects of combination of 2C1 and 3D6 in PDX (patient-derived xenograft).

FIG. 14 shows the effects of 2C1 and 3D6 combination in PDX.

SEQUENCE LISTING

```
Sequence total quantity: 42
SEQ ID NO: 1            moltype = DNA   length = 24
FEATURE                 Location/Qualifiers
misc_feature            1..24
                        note = mAb 2C1 CDR1 Heavy Chain DNA
source                  1..24
                        mol_type = other DNA
```

```
                                organism = synthetic construct
SEQUENCE: 1
gggttcacct tcagtgattt ctat                                                      24

SEQ ID NO: 2              moltype = AA  length = 8
FEATURE                   Location/Qualifiers
REGION                    1..8
                          note = mAb 2C1 CDR1 Heavy Chain Protein
source                    1..8
                          mol_type = protein
                          organism = synthetic construct
SEQUENCE: 2
GFTFSDFY                                                                         8

SEQ ID NO: 3              moltype = DNA  length = 30
FEATURE                   Location/Qualifiers
misc_feature              1..30
                          note = mAb 2C1 CDR2 Heavy Chain DNA
source                    1..30
                          mol_type = other DNA
                          organism = synthetic construct
SEQUENCE: 3
agtaaaaaca aagctaatga ttatacaaca                                                30

SEQ ID NO: 4              moltype = AA  length = 10
FEATURE                   Location/Qualifiers
REGION                    1..10
                          note = mAb 2C1 CDR2 Heavy Chain Protein
source                    1..10
                          mol_type = protein
                          organism = synthetic construct
SEQUENCE: 4
SKNKANDYTT                                                                      10

SEQ ID NO: 5              moltype = DNA  length = 45
FEATURE                   Location/Qualifiers
misc_feature              1..45
                          note = mAb 2C1 CDR3 Heavy Chain DNA
source                    1..45
                          mol_type = other DNA
                          organism = synthetic construct
SEQUENCE: 5
gccgctgggg gttacgacga gggagttggc tggtacttcg atgtc                                45

SEQ ID NO: 6              moltype = AA  length = 15
FEATURE                   Location/Qualifiers
REGION                    1..15
                          note = mAb 2C1 CDR3 Heavy Chain Protein
source                    1..15
                          mol_type = protein
                          organism = synthetic construct
SEQUENCE: 6
AAGGYDEGVG WYFDV                                                                15

SEQ ID NO: 7              moltype = DNA  length = 18
FEATURE                   Location/Qualifiers
misc_feature              1..18
                          note = mAb 2C1 CDR1 Light Chain DNA
source                    1..18
                          mol_type = other DNA
                          organism = synthetic construct
SEQUENCE: 7
cagaatgtgg gtactaat                                                             18

SEQ ID NO: 8              moltype = AA  length = 6
FEATURE                   Location/Qualifiers
REGION                    1..6
                          note = mAb 2C1 CDR1 Light Chain Protein
source                    1..6
                          mol_type = protein
                          organism = synthetic construct
SEQUENCE: 8
QNVGTN                                                                           6

SEQ ID NO: 9              moltype =      length =
SEQUENCE: 9
000

SEQ ID NO: 10             moltype =      length =
```

-continued

```
SEQUENCE: 10
000

SEQ ID NO: 11            moltype = DNA  length = 27
FEATURE                  Location/Qualifiers
misc_feature             1..27
                         note = mAb 2C1 CDR3 Light Chain DNA
source                   1..27
                         mol_type = other DNA
                         organism = synthetic construct
SEQUENCE: 11
cagcaatata ataactatcc gtacacg                                         27

SEQ ID NO: 12            moltype = AA  length = 9
FEATURE                  Location/Qualifiers
REGION                   1..9
                         note = mAb 2C1 CDR3 Light Chain Protein
source                   1..9
                         mol_type = protein
                         organism = synthetic construct
SEQUENCE: 12
QQYNNYPYT                                                              9

SEQ ID NO: 13            moltype = DNA  length = 24
FEATURE                  Location/Qualifiers
misc_feature             1..24
                         note = mAb 3G4 CDR1 Heavy Chain DNA
source                   1..24
                         mol_type = other DNA
                         organism = synthetic construct
SEQUENCE: 13
ggctacacct tcactaacta ctgg                                            24

SEQ ID NO: 14            moltype = AA  length = 8
FEATURE                  Location/Qualifiers
REGION                   1..8
                         note = mAb 3G4 CDR1 Heavy Chain Protein
source                   1..8
                         mol_type = protein
                         organism = synthetic construct
SEQUENCE: 14
GYTFTNYW                                                               8

SEQ ID NO: 15            moltype = DNA  length = 24
FEATURE                  Location/Qualifiers
misc_feature             1..24
                         note = mAb 3G4 CDR2 Heavy Chain DNA
source                   1..24
                         mol_type = other DNA
                         organism = synthetic construct
SEQUENCE: 15
gtttaccctg gaggtggtta tatt                                            24

SEQ ID NO: 16            moltype = AA  length = 8
FEATURE                  Location/Qualifiers
REGION                   1..8
                         note = mAb 3G4 CDR2 Heavy Chain Protein
source                   1..8
                         mol_type = protein
                         organism = synthetic construct
SEQUENCE: 16
VYPGGGYI                                                               8

SEQ ID NO: 17            moltype = DNA  length = 39
FEATURE                  Location/Qualifiers
misc_feature             1..39
                         note = mAb 3G4 CDR3 Heavy Chain DNA
source                   1..39
                         mol_type = other DNA
                         organism = synthetic construct
SEQUENCE: 17
gcaagatggg ggactacggt cgactggtac ttcgatgtc                            39

SEQ ID NO: 18            moltype = AA  length = 13
FEATURE                  Location/Qualifiers
REGION                   1..13
                         note = mAb 3G4 CDR3 Heavy Chain Protein
source                   1..13
                         mol_type = protein
```

```
                              organism = synthetic construct
SEQUENCE: 18
ARWGTTVDWY FDV                                                           13

SEQ ID NO: 19           moltype = DNA  length = 15
FEATURE                 Location/Qualifiers
misc_feature            1..15
                        note = mAb 3G4 CDR1 Light Chain DNA
source                  1..15
                        mol_type = other DNA
                        organism = synthetic construct
SEQUENCE: 19
tcaagtgtaa gttac                                                         15

SEQ ID NO: 20           moltype = AA  length = 5
FEATURE                 Location/Qualifiers
REGION                  1..5
                        note = mAB 3G4 CDR1 Light Chain Protein
source                  1..5
                        mol_type = protein
                        organism = synthetic construct
SEQUENCE: 20
SSVSY                                                                     5

SEQ ID NO: 21           moltype =   length =
SEQUENCE: 21
000

SEQ ID NO: 22           moltype =   length =
SEQUENCE: 22
000

SEQ ID NO: 23           moltype = DNA  length = 27
FEATURE                 Location/Qualifiers
misc_feature            1..27
                        note = mAb 3G4 CDR3 Light Chain DNA
source                  1..27
                        mol_type = other DNA
                        organism = synthetic construct
SEQUENCE: 23
cagcagtgga gtagtaaccc atacacg                                            27

SEQ ID NO: 24           moltype = AA  length = 9
FEATURE                 Location/Qualifiers
REGION                  1..9
                        note = mAb 3G4 CDR3 Light Chain DNA
source                  1..9
                        mol_type = protein
                        organism = synthetic construct
SEQUENCE: 24
QQWSSNPYT                                                                 9

SEQ ID NO: 25           moltype = DNA  length = 24
FEATURE                 Location/Qualifiers
misc_feature            1..24
                        note = mAb 3D6 CDR1 Heavy Chain DNA
source                  1..24
                        mol_type = other DNA
                        organism = synthetic construct
SEQUENCE: 25
ggattcactt tcagtgacta tgac                                               24

SEQ ID NO: 26           moltype = AA  length = 8
FEATURE                 Location/Qualifiers
REGION                  1..8
                        note = mAb 3D6 CDR1 Heavy Chain Protein
source                  1..8
                        mol_type = protein
                        organism = synthetic construct
SEQUENCE: 26
GFTFSDYD                                                                  8

SEQ ID NO: 27           moltype = DNA  length = 24
FEATURE                 Location/Qualifiers
misc_feature            1..24
                        note = mAb 3D6 CDR2 Heavy Chain DNA
source                  1..24
                        mol_type = other DNA
                        organism = synthetic construct
```

```
SEQUENCE: 27
attagtgatg gtggtagttt cacc                                              24

SEQ ID NO: 28              moltype = AA  length = 8
FEATURE                    Location/Qualifiers
REGION                     1..8
                           note = mAb 3D6 CDR2 Heavy Chain Protein
source                     1..8
                           mol_type = protein
                           organism = synthetic construct
SEQUENCE: 28
ISDGGSFT                                                                 8

SEQ ID NO: 29              moltype = DNA  length = 36
FEATURE                    Location/Qualifiers
misc_feature               1..36
                           note = mAb 3D6 CDR3 Heavy Chain DNA
source                     1..36
                           mol_type = other DNA
                           organism = synthetic construct
SEQUENCE: 29
gcaaaaaaga agggctatgg tgatgctatg gactac                                 36

SEQ ID NO: 30              moltype = AA  length = 12
FEATURE                    Location/Qualifiers
REGION                     1..12
                           note = mAb 3D6 CDR3 Heavy Chain Protein
source                     1..12
                           mol_type = protein
                           organism = synthetic construct
SEQUENCE: 30
AKKKGYGDAM DY                                                           12

SEQ ID NO: 31              moltype = DNA  length = 18
FEATURE                    Location/Qualifiers
misc_feature               1..18
                           note = mAb 3D6 CDR1 Light Chain DNA
source                     1..18
                           mol_type = other DNA
                           organism = synthetic construct
SEQUENCE: 31
gaggacattt ttattcgg                                                     18

SEQ ID NO: 32              moltype = AA  length = 6
FEATURE                    Location/Qualifiers
REGION                     1..6
                           note = mAb 3D6 CDR1 Light Chain Protein
source                     1..6
                           mol_type = protein
                           organism = synthetic construct
SEQUENCE: 32
EDIFIR                                                                   6

SEQ ID NO: 33              moltype =     length =
SEQUENCE: 33
000

SEQ ID NO: 34              moltype =     length =
SEQUENCE: 34
000

SEQ ID NO: 35              moltype = DNA  length = 27
FEATURE                    Location/Qualifiers
misc_feature               1..27
                           note = mAb 3D6 CDR3 Light Chain DNA
source                     1..27
                           mol_type = other DNA
                           organism = synthetic construct
SEQUENCE: 35
caacagtatt ggaatactcc gtggacg                                           27

SEQ ID NO: 36              moltype = AA  length = 9
FEATURE                    Location/Qualifiers
REGION                     1..9
                           note = mAb 3D6 CDR3 Light Chain Protein
source                     1..9
                           mol_type = protein
                           organism = synthetic construct
SEQUENCE: 36
```

```
QQYWNTPWT                                                                           9

SEQ ID NO: 37           moltype = AA  length = 130
FEATURE                 Location/Qualifiers
REGION                  1..130
                        note = 2C1 Heavy Chain
VARIANT                 10
                        note = Xaa can be any naturally occurring amino acid
VARIANT                 31..34
                        note = Xaa can be any naturally occurring amino acid
VARIANT                 41..44
                        note = Any amino acid or absent
VARIANT                 73
                        note = Xaa can be any naturally occurring amino acid
source                  1..130
                        mol_type = protein
                        organism = synthetic construct
SEQUENCE: 37
EVKLVESGGX GLVQPGGSLR LSCAISGFTF XXXXSDFYME WVRQFPGKRL EWVAASKNKA        60
NDYTTEYSAS VKXGRFIVSR DTSQSILYLQ MNALRAEDTA IYYCAAGGYD EGVGWYFDVW       120
GAGTTVTVSS                                                             130

SEQ ID NO: 38           moltype = AA  length = 128
FEATURE                 Location/Qualifiers
REGION                  1..128
                        note = mAb 2C1 Light Chain Full Protein
VARIANT                 30..35
                        note = Xaa can be any naturally occurring amino acid
VARIANT                 40..45
                        note = Any amino acid or absent
VARIANT                 58..64
                        note = Any amino acid or absent
VARIANT                 73
                        note = Xaa can be any naturally occurring amino acid
VARIANT                 81..82
                        note = Xaa can be any naturally occurring amino acid
VARIANT                 110..113
                        note = Any amino acid or absent
VARIANT                 128
                        note = Xaa can be any naturally occurring amino acid
source                  1..128
                        mol_type = protein
                        organism = synthetic construct
SEQUENCE: 38
DIVMTQSQKF MSTSVGDRVS VTCKASQNVX XXXXXGTNVA WFQQKPGLSP KPLIYSAXXX        60
XXXXSYRYRG VPXDRFTGSA XXSGTDFTLT ISSVQSEDLA EYFCQQYNNX XXXYPYTFGG       120
GTRLEINX                                                               128

SEQ ID NO: 39           moltype = AA  length = 128
FEATURE                 Location/Qualifiers
REGION                  1..128
                        note = mAb 3G4 Heavy Chain Full Protein
VARIANT                 10
                        note = Xaa can be any naturally occurring amino acid
VARIANT                 31..34
                        note = Xaa can be any naturally occurring amino acid
VARIANT                 41..44
                        note = Any amino acid or absent
VARIANT                 60..61
                        note = Any amino acid or absent
VARIANT                 73
                        note = Xaa can be any naturally occurring amino acid
source                  1..128
                        mol_type = protein
                        organism = synthetic construct
SEQUENCE: 39
QVQLQQSGAX ELVRPGTSVK ISCKASGYTF XXXXTNYWLG WVKQRPGHGL EWIGDVYPGX        60
XGGYINYNEK FKXGKATLTA DTSSSTAYMQ LSSLTSEDSA VYFCARWGTT VDWYFDVWGA      120
GTTVTVSS                                                               128

SEQ ID NO: 40           moltype = AA  length = 128
FEATURE                 Location/Qualifiers
REGION                  1..128
                        note = mAb 3G4 Light Chain Full Protein
VARIANT                 30..36
                        note = Any amino acid or absent
VARIANT                 58..64
                        note = Any amino acid or absent
VARIANT                 73
```

```
                        note = Xaa can be any naturally occurring amino acid
VARIANT                 81..82
                        note = Xaa can be any naturally occurring amino acid
VARIANT                 110..113
                        note = Any amino acid or absent
VARIANT                 128
                        note = Xaa can be any naturally occurring amino acid
source                  1..128
                        mol_type = protein
                        organism = synthetic construct
SEQUENCE: 40
QIVLTQSPAI MSASPGEKVT MTCSASSSVX XXXXXXSYMH WYQQKSGTSP KRWIYDTXXX   60
XXXXSKLASG VPXARFSGSG XXSGTSYSLT ISSMEAEDAA TYYCQQWSSX XXXNPYTFGG  120
GTKLEIKX                                                          128

SEQ ID NO: 41           moltype = AA  length = 128
FEATURE                 Location/Qualifiers
REGION                  1..128
                        note = mAb 3D6 Heavy Chain Full Protein
VARIANT                 10
                        note = Xaa can be any naturally occurring amino acid
VARIANT                 31..34
                        note = Any amino acid or absent
VARIANT                 60..61
                        note = Any amino acid or absent
VARIANT                 73
                        note = Xaa can be any naturally occurring amino acid
VARIANT                 111
                        note = Any amino acid or absent
source                  1..128
                        mol_type = protein
                        organism = synthetic construct
SEQUENCE: 41
EVHLVESGGX GLVKPGGSLQ VSCAASGFTF XXXXSDYDMF WVRQTPEKRL EWVATISDGX   60
XGSFTYYPDS VKXGRFTISR DNAKNNLYLQ MSSLKSEDTA IYYCAKKKGY XGDAMDYWGQ  120
GTSVTVSS                                                          128

SEQ ID NO: 42           moltype = AA  length = 128
FEATURE                 Location/Qualifiers
REGION                  1..128
                        note = mAb 3D6 Light Chain Full Protein
VARIANT                 30..35
                        note = Any amino acid or absent
VARIANT                 58..64
                        note = Any amino acid or absent
VARIANT                 73
                        note = Xaa can be any naturally occurring amino acid
VARIANT                 81..82
                        note = Xaa can be any naturally occurring amino acid
VARIANT                 110..113
                        note = Any amino acid or absent
VARIANT                 128
                        note = Xaa can be any naturally occurring amino acid
source                  1..128
                        mol_type = protein
                        organism = synthetic construct
SEQUENCE: 42
DIQMTQSSSS FSVSLGDRVT ITCKASEDIX XXXXXFIRLA WYQQKPGNAP RLLISGAXXX   60
XXXXTSLETG VPXSRFSGSG XXSGKDYTLS ITSLQTEDVA TYYCQQYWNX XXXTPWTFGG  120
GTKLDFKX                                                          128
```

The invention claimed is:

1. An antibody which binds annexin A1, or an annexin A1-binding fragment thereof, or an annexin A1-binding fusion protein, comprising: a) a heavy chain comprising: CDR1 comprising the amino acid sequence in SEQ ID NO:2; CDR2 comprising the amino acid sequence in SEQ ID NO:4; CDR3 comprising the amino acid sequence in SEQ ID NO:6; and a light chain comprising: comprising the amino acid sequence in SEQ ID NO:8; CDR2 comprising the amino acid sequence SAS, SEQ ID NO:10; CDR3 comprising the amino acid sequence in SEQ ID NO:12; or b) a heavy chain comprising: CDR1 comprising the amino acid sequence in SEQ ID NO:14; CDR2 comprising the amino acid sequence in SEQ ID NO:16; CDR3 comprising the amino acid sequence in SEQ ID NO:18; and a light chain comprising: CDR1 comprising the amino acid sequence in SEQ ID NO:20; CDR2 comprising the amino acid sequence DTS, SEQ ID NO:22; CDR3 comprising the amino acid sequence in SEQ ID NO:24; or c) a heavy chain comprising: CDR1 comprising the amino acid sequence in SEQ ID NO:26; CDR2 comprising the amino acid sequence in SEQ ID NO:28; CDR3 comprising the amino acid sequence in SEQ ID NO:30; and a light chain comprising: CDR1 comprising the amino acid sequence in SEQ ID NO:32; CDR2 comprising the amino acid sequence GAT, SEQ ID NO:34; CDR3 comprising the amino acid sequence in SEQ ID NO:36.

2. The antibody, annexin A1-binding fragment, or fusion protein of claim 1, wherein the heavy chain comprising: CDR1 comprising the amino acid sequence in SEQ ID NO:2; CDR2 comprising the amino acid sequence in SEQ ID NO:4; CDR3 comprising the amino acid sequence in SEQ ID NO:6; and a light chain comprising: comprising the amino acid sequence in SEQ ID NO:8; CDR2 having the sequence SAS, SEQ ID NO:10; CDR3 comprising the amino acid sequence in SEQ ID NO:12.

3. The antibody of claim 1, wherein the antibody is a monoclonal antibody.

4. The antibody, annexin A1-binding fragment, or fusion protein of claim 1, comprising framework regions of a light chain and/or a heavy chain which are human framework regions, or have 85% or more sequence identity thereto.

5. The antibody, annexin A1-binding fragment, or fusion protein of claim 4, wherein the framework regions of the light chain and/or the heavy chain are human framework regions.

6. The antibody of claim 1, wherein the antibody is a humanized antibody.

7. The antibody or annexin A1-binding fragment of claim 1, wherein the antibody or antigen-binding fragment thereof has a human sequence Fc region.

8. A nucleic acid encoding a heavy chain of claim 1.

9. A nucleic acid encoding a light chain of claim 1.

10. The nucleic acid of claim 8, which is an expression vector.

11. An antibody which binds annexin A1 comprising the complementary-determining regions (CDRs), wherein each of the CDRs has an amino acid sequence as follows: CDR1 comprising the amino acid sequence in SEQ ID NO: 2; CDR2 comprising the amino acid sequence in SEQ ID NO: 4; CDR3 comprising the amino acid sequence in SEQ ID NO: 6; CDR4 comprising the amino acid sequence in SEQ ID NO: 8; CDR5 comprising the amino acid sequence SAS, SEQ ID NO:10; and CDR6 comprising the amino acid sequence in SEQ ID NO: 12.

12. The antibody of claim 11, wherein the antibody is a monoclonal antibody.

\* \* \* \* \*